US012677819B2

(12) United States Patent
Deljkovic et al.

(10) Patent No.: US 12,677,819 B2
(45) Date of Patent: Jul. 14, 2026

(54) TALL PLANT HEALTH MANAGEMENT SYSTEM

(71) Applicant: CROPSY TECHNOLOGIES LIMITED, Auckland (NZ)

(72) Inventors: Leila Deljkovic, Auckland (NZ); Ali Sarmad Saieb Al-Omari, Auckland (NZ); Winston Su, Auckland (NZ); Rory Douglas Buchanan, Auckland (NZ)

(73) Assignee: CROPSY TECHNOLOGIES LIMITED, Auckland (NZ)

( * ) Notice: Subject to any disclaimer, the term of this patent is extended or adjusted under 35 U.S.C. 154(b) by 360 days.

(21) Appl. No.: 17/800,817

(22) PCT Filed: Feb. 19, 2021

(86) PCT No.: PCT/NZ2021/050018
§ 371 (c)(1),
(2) Date: Aug. 18, 2022

(87) PCT Pub. No.: WO2021/167470
PCT Pub. Date: Aug. 26, 2021

(65) Prior Publication Data
US 2023/0079259 A1 Mar. 16, 2023

(30) Foreign Application Priority Data
Feb. 20, 2020 (NZ) ........................................ 761912

(51) Int. Cl.
*G01N 21/84* (2006.01)
*A01M 7/00* (2006.01)
(Continued)

(52) U.S. Cl.
CPC ........ *A01M 7/0089* (2013.01); *A01M 21/043* (2013.01); *G01N 21/21* (2013.01);
(Continued)

(58) Field of Classification Search
CPC .. A01M 7/0089; A01M 21/043; G01N 21/21; G01N 33/0098; G01N 2021/8466;
(Continued)

(56) References Cited

U.S. PATENT DOCUMENTS 5,835,206 A * 11/1998 Tragesser ............... G01N 21/25
356/406
6,052,187 A 4/2000 Krishnan et al.
(Continued)

FOREIGN PATENT DOCUMENTS

EP 2107361 A1 10/2009
KR 1020090127393 A 12/2009
(Continued)

OTHER PUBLICATIONS

Stephen Nuske et al.: "Automated Visual Yield Estimation in Vineyards", Journal of Field Robotics, vol. 31, No. 5, Aug. 11, 2014, pp. 837-860, XP055263684, US ISSN: 1556-4959, DOI: 10.1002/rob.21541 *the whole document*.
(Continued)

*Primary Examiner* — Huy C Ho
(74) *Attorney, Agent, or Firm* — JCIP; Joseph G. Chu

(57) ABSTRACT

A method comprising: activating a strobed or pulsed illumination source to produce illuminating light; polarising the illuminating light in a first polarisation axis; illuminating at least part of a tall plant crop with the polarised illuminating light to produce reflected illuminating light; polarising the reflected illuminating light in a second polarisation axis transverse to the first polarisation axis to produce cross-polarised reflected illuminating light; capturing an image of at least part of the tall plant crop using the cross-polarised reflected illuminating light; and analysing the captured image to determine a condition of the tall plant crop. Also a
(Continued)

vehicle mounted image capture system, a vehicle mounted spraying system and a plant health management system.

20 Claims, 33 Drawing Sheets

(51) Int. Cl.

| | |
|---|---|
| *A01M 21/04* | (2006.01) |
| *G01N 21/21* | (2006.01) |
| *G01N 33/00* | (2006.01) |
| *G03B 15/05* | (2021.01) |
| *G06V 20/10* | (2022.01) |

(52) U.S. Cl.
CPC ......... *G01N 33/0098* (2013.01); *G03B 15/05* (2013.01); *G06V 20/188* (2022.01); *G01N 2021/8466* (2013.01)

(58) Field of Classification Search
CPC ...................... G03B 15/05; G03B 2215/0589; G03B 15/03; G03B 11/00; G06V 20/188; F21V 29/52; F21V 29/54
USPC ......................................................... 382/110
See application file for complete search history.

(56) References Cited

U.S. PATENT DOCUMENTS

| | | |
|---|---|---|
| 6,964,501 B2 | 11/2005 | Ryan |
| 2002/0024665 A1 | 2/2002 | Masten |
| 2010/0324830 A1 | 12/2010 | Solie et al. |
| 2015/0204787 A1 | 7/2015 | Kramer et al. |
| 2016/0113503 A1 | 4/2016 | Benaron |
| 2017/0131200 A1 | 5/2017 | Raveh et al. |
| 2018/0129894 A1 | 5/2018 | Nuske et al. |
| 2018/0330165 A1 | 11/2018 | Halligan et al. |
| 2019/0098842 A1 | 4/2019 | Barber, III et al. |
| 2022/0330468 A1* | 10/2022 | Underwood ......... G06V 20/188 |

FOREIGN PATENT DOCUMENTS

| | | |
|---|---|---|
| WO | 2018122242 A2 | 7/2018 |
| WO | 2019014703 A1 | 1/2019 |

OTHER PUBLICATIONS

Oberti Roberto et al: "Selective spraying of grapevines for disease control using a modular agricultural robot", Biosystems Engineering, Elsevier, Amsterdam, NL, vol. 146, Jan. 13, 2016 (Jan. 13, 2016), pp. 203-215, XP029597690, ISSN: 1537-5110, DOI: 10.1016/J.BIOSYSTEMSENG.2015.12.004 *the whole document*.

Nguyen-Do-Trong Nghia et al: "Cross-polarised VNIR hyperspectral reflectance imaging system for agrifood products", Biosystems Engineering, Elsevier, Amsterdam, NL, vol. 151, Sep. 29, 2016 (Sep. 29, 2016), pp. 152-157, XP029820583, ISSN: 1537-5110, DOI: 10.1016/J.BIOSYSTEMSENG.2016.08.027 *Abstract; Chapter 4. Conclusions; Figure 3*.

D A Shaikh et al: "Intelligent Autonomous Farming Robot with Plant Disease Detection using Image Processing", International Journal of Advanced Research in Computer and Communiction Engineering, vol. 5, No. 4, Apr. 1, 2016 (Apr. 1, 2016), pp. 1012-1016, XP055466047, India ISSN: 2319-5940, DOI: 10.17148/IJARCCE.2016.54248 *Abstract and Conclusion*.

Extended European Search Report dated Feb. 1, 2024 for European Application No. 21756571.2.

International Search Report and Written Opinion of International Searching Authority dated May 24, 2021 for International Application No. PCT/NZ2021/050018.

Kenji O. et al., "3D lidar imaging for detecting and understanding plant responses and canopy structure", Journal of Experimental Botany, vol. 58, No. 4, 2007, pp. 881-898. Fig. 1 and the associated text.

Paulus S., "Measuring crops in 3D: using geometry for plant phenotyping", Plant Methods, Review article, 15 (103), Sep. 3, 2019, document obtained from internet; https://plantmethods.biomedcentral.com/articles/10.1186/13007-019-0490-0 Fig. 1, and the associated part.

Cañada-Cañada F. et al., "Laser-Induced Fluorescence Imaging System for Weather Stress Analysis in Plant Leaves of Different Wheat Varieties", Chemia Analityczna (Warsaw), 53, Jan. 2008, pp. 545-556. Fig. 2, Experimental part, pp. 548-549.

* cited by examiner

605

606

702

112

710

706

712

704

708

714

▪ ▪ ▪ ▪ ▪ ▪ = CONTROL SIGNAL

Post-Operation

Insights

Detections               Treatment

Pest and Disease Spread Trend

Spray Summary - amount used, saved

Pest and Disease History and Progression

Current Spray Approach Efficacy

Locations of Pest and Disease Over Time

Locations, Type, and concentration of Spray

Infection/Infestation Information

Treatment Information

Turn Off Cropsy's System

Upload Data to the Cloud

Utilise Insights to Improve Processes

Grower

IF DATA IS ON USB

IF DATA IS ON PHONE

Disconnect USB Flash Drive

Connect Phone to Internet

Connect USB Flash Drive to PC

Connect to Base Station

Launch Cropsy App

Launch Cropsy App

Data Uploaded

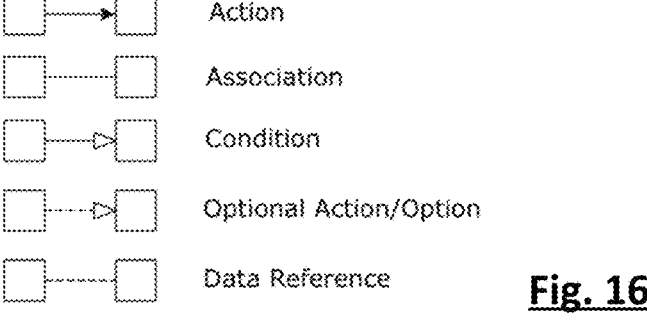

├──▶ Action

├──── Association

├──▷ Condition

├----▷ Optional Action/Option

├----- Data Reference

Leaf Blower

Fig. 30

TALL PLANT HEALTH MANAGEMENT SYSTEM

FIELD

This invention relates to a tall plant health management system.

BACKGROUND

Various types of machine vision systems exist. In relation to management of plant health, there are some examples of the use of machine vision in detecting diseases or pests in short crops.

Machine vision use in short crops is not without problems. For example: limited annotated datasets, symptom representation, covariate shift, image background, image capture conditions, symptom segmentation, symptom variations, simultaneous disorders solved, disorders with similar symptoms and/or specular lighting.

One of the more problematic image capture conditions is ambient illumination, in particular the variable effect of the sun on the image data set. The variable effect of the sun can prove challenging to overcome in a commercial setting.

Machine vision systems in use may also lack the ability to image details and surface features of plants from a close distance.

SUMMARY

According to one example embodiment there is provided a method of health management of tall plant crop grown using a training system comprising activating a strobed or pulsed illumination source to produce illuminating light, polarising the illuminating light in a first polarisation axis, illuminating at least part of a tall plant crop with the polarised illuminating light to produce reflected illuminating light, polarising the reflected illuminating light in a second polarisation axis transverse to the first polarisation axis to produce cross-polarised reflected illuminating light, capturing an image of at least part of the tall plant crop using the cross-polarised reflected illuminating light, and analysing the captured image to determine a condition of the tall plant crop.

According to one example embodiment, there is provided a vehicle-mountable system for health management of tall plant crop grown using a training system, said system comprising an active illumination source configured to produce illuminating light to illuminate a tall plant crop, a first polariser arranged to polarise the illuminating light from the active illumination source, a second polariser arranged to cross-polarise light reflected from the tall plant crop, the second polariser having a polarisation axis transverse to the polarisation axis of the first polariser, an image capture device configured to capture light cross-polarised by the second polariser, and an on-board computation unit configured to process images of the light cross-polarised by the second polariser captured by the image capture device in real-time. The active illumination source is configured to produce illuminating light of sufficient intensity such that the cross-polarised reflected illuminating light is of greater intensity than ambient light reflected from the tall plant crop and polarised by the second polariser.

According to on example embodiment, there is provided a system for health management of tall plant crop grown using a training system, said system comprising a vehicle-mountable arrangement comprising a polarised high intensity illumination source configured to illuminate foliage or fruit of a target tall plant crop at a plurality of locations along or of said tall plant crop, and a polarised image capture device configured to capture images of the foliage and/or fruit illuminated at said plurality of locations, said high intensity illumination source and image capture device polarised with polarisers oriented transverse to one another, and an on-board computation unit configured to process images of the illuminated foliage and/or fruit in real-time together with high accuracy location data to form tall plant image data, and determine a feature of at least part of the tall plant crop at at least one location of the plurality of locations along or of said tall plant crop based on analysis of said tall plant image data. The system is configured to determine and recommend plant health management actions for the tall plant crop based on said feature, wherein said feature comprises any one or more of: yield, pests or disease present on and/or effecting the tall plant crop, location and number of canes, spurs, and/or branches on the tall plant crop, growth stage or maturity of the foliage and/or fruit the tall plant crop, nutritional deficiencies, location and number of plant suckers, location and number of healthy, and limp and/or damaged shoots, canopy density and/or leaf-area index, location and number of untreated pruning cuts and/or moisture level.

Embodiments may be implemented according to any one of the dependent claims.

It is acknowledged that the terms "comprise", "comprises" and "comprising" may, under varying jurisdictions, be attributed with either an exclusive or an inclusive meaning. For the purpose of this specification, and unless otherwise noted, these terms are intended to have an inclusive meaning—i.e., they will be taken to mean an inclusion of the listed components which the use directly references, and possibly also of other non-specified components or elements.

Reference to any document in this specification does not constitute an admission that it is prior art, validly combinable with other documents or that it forms part of the common general knowledge.

BRIEF DESCRIPTION OF THE DRAWINGS

The accompanying drawings which are incorporated in and constitute part of the specification, illustrate embodiments of the invention and, together with the general description of the invention given above, and the detailed description of embodiments given below, serve to explain the principles of the invention, in which:

FIGS. 6b to 6e are perspective views of four possible implementations of the leaf blowers in FIG. 6a;

FIG. 7 is a schematic diagram of the sprayer system in FIG. 2;

FIG. 16 is a use-case diagram specifying user interaction following a detection/treatment session;

FIG. 30 is a flow chart of a leaf blower control algorithm according to one example embodiment.

DETAILED DESCRIPTION

In order to reduce the effect of variability of sun illumination on short crop machine vision, one option is to use a sun shield. In that case the cameras might be generally downward facing, for example, seeing a bird's-eye-view. The cameras and spraying system may be integrated into a tractor attachment. However, employing a sun shield for plant species, other than short crops, may prove commercially challenging in some applications. In other words, an alternative solution may be required in some applications.

Depending on the application, embodiments may seek to improve image capture of "tall crops" or "tall plants", as opposed to "short crops". Depending on the application, the distinction between short and tall may differ. Some indicia of a tall crop may include:

Mostly woody trees or vines grown in distinct rows;

Narrow in width as opposed to full and bushy, such that the camera may capture sufficiently large areas of the foliage from either side of the row while viewing the foliage from the side, or that any fruit or produce from the plant could not effectively be seen from above;

Grown vertically with supports or training systems such as posts, trellises, wires, ties, bindings, etc. Short or bushy crops generally aren't "trained".

Grown using training systems that create a flat, narrow canopy; and/or

Applications where the camera must be facing sideways generally indicate that a crop is too tall to be covered easily, otherwise a camera could look down on the crop, and it could be covered with a sun shield.

Figure 1:
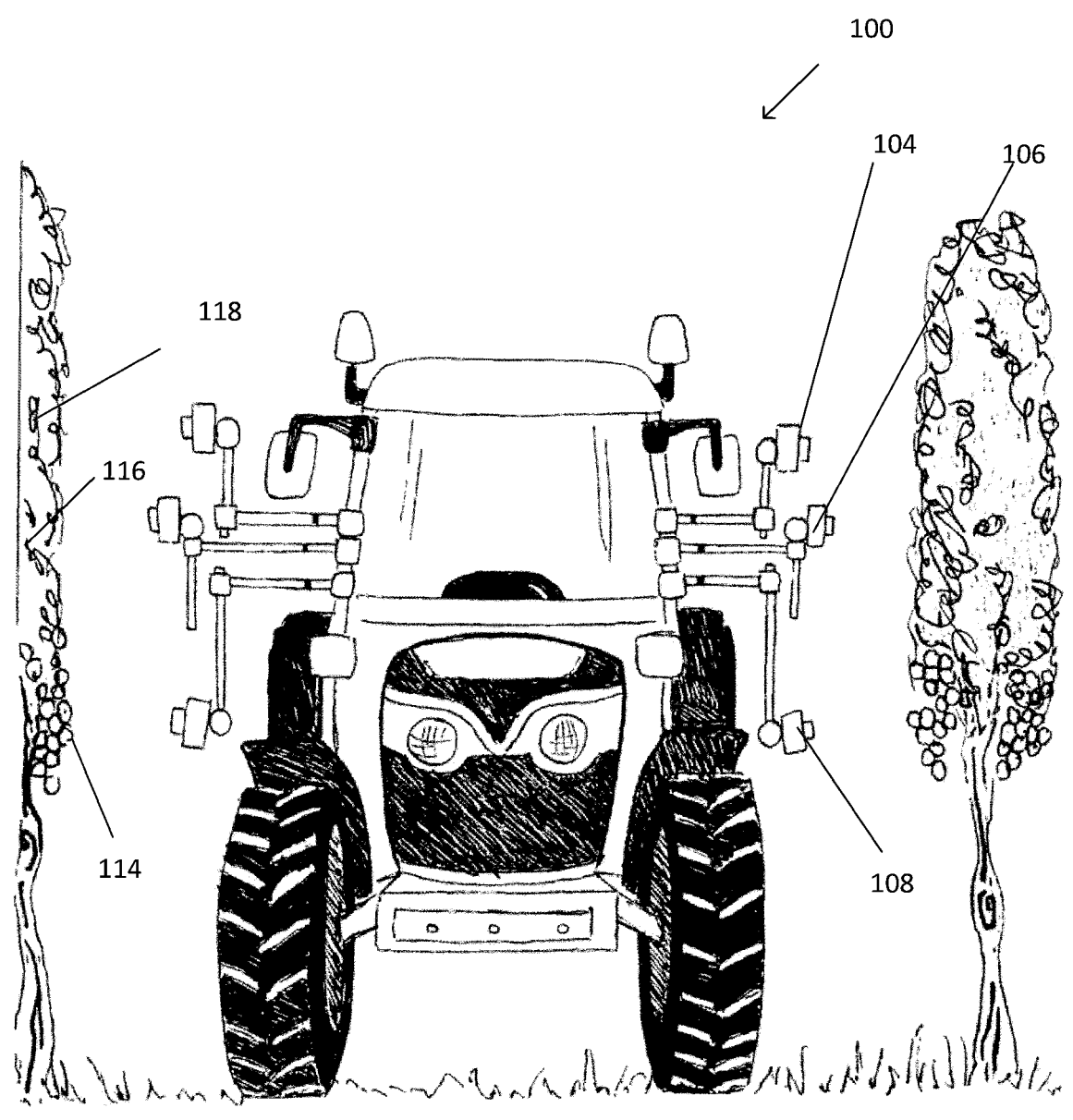
FIG. 1 is a front view of a tractor including an image capture system according to an example embodiment.
Figure 2:
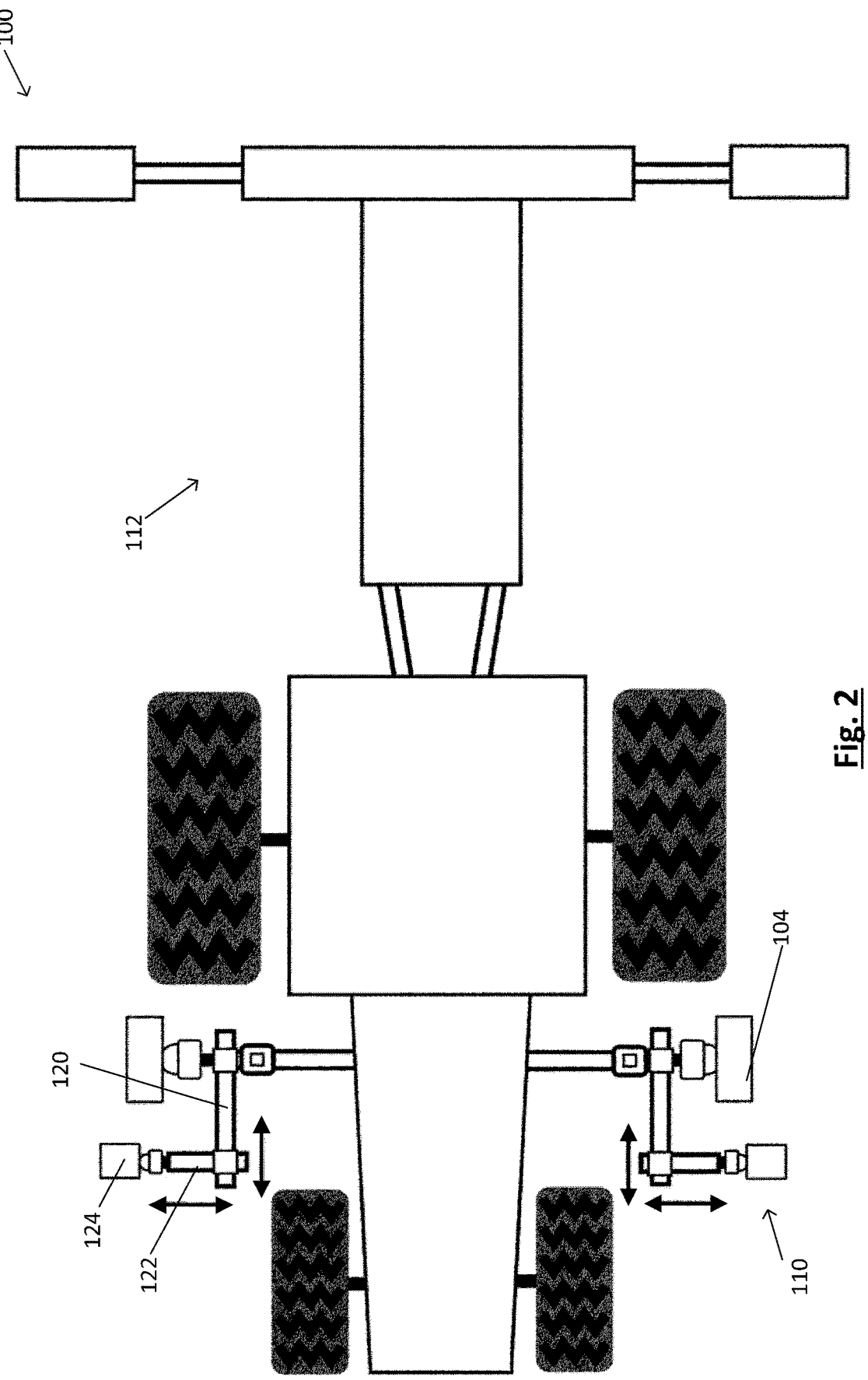
FIG. 2 is a plan view of the tractor in FIG. 1 including an automated spraying system and a blower.

FIGS. 1 and 2 illustrate a vehicle mounted image capture and analysis system 100 according to an example embodiment. The main components include an illumination source, multiple image capture devices 104, 106, 108, a blower 110 to displace the foliage and/or produce. It may include an automated spray system 112 to spray based on the results of the image capture, or other output application modules.

Depending on the application, vehicle mounted may mean that the vehicle itself is multipurpose, such as a tractor or all-terrain vehicle, and the image capture devices can be detached if the vehicle needs to be used for other purposes. This is as opposed to a purpose designed vehicle or robot just for capturing images or analysing images.

Image Capture

Figure 3A:
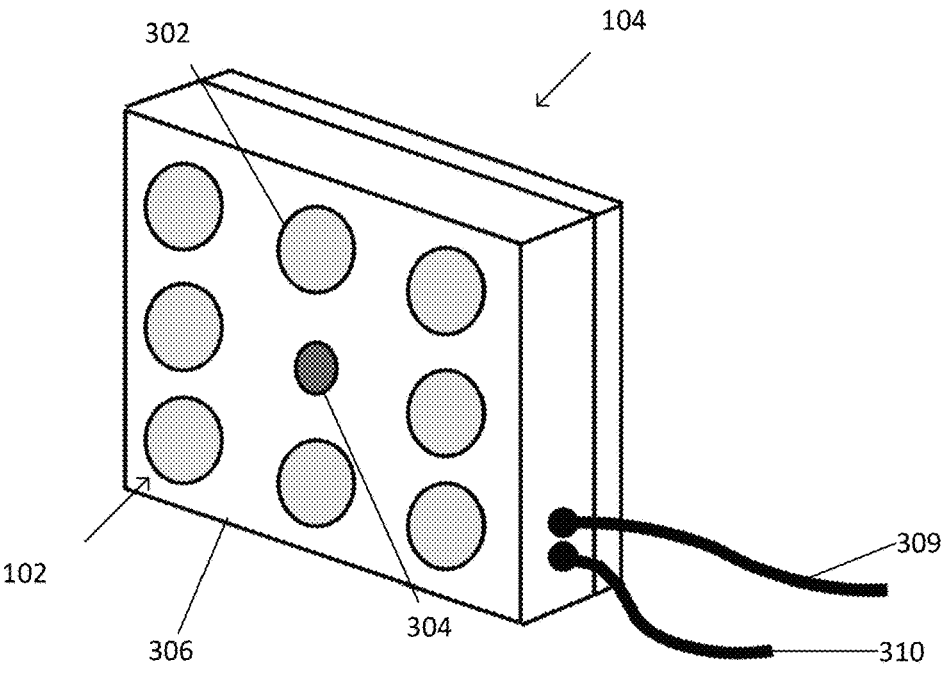
FIG. 3a is a perspective view of the image capture device in FIG. 1 without a spray shield.
Figure 3B:
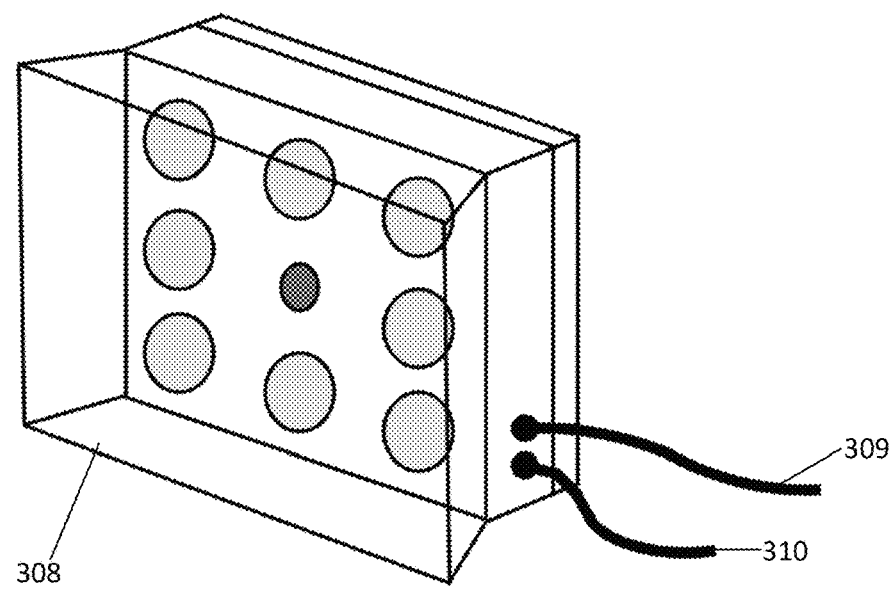
FIG. 3b is a perspective view of the image capture device in FIG. 1 with a spray shield.

An example image capture device 104 is shown in FIGS. 3a and 3b. An illumination source 102, may take the form of 8 LEDs 302, and the LEDs 302 may surround a CMOS sensor 304 in the centre of a housing 306. Surrounding the imaging component with the lighting components improves the evenness and consistent distribution of light in the captured image. This is also a compact way of achieving evenness and consistent distribution. Generally speaking, the closer the origin of light is to the imaging device, the closer the field of the view of the imaging device will be to the illumination field of the lighting device. Consequently, the more homogenous and consistent the lighting in the collected images will be, regardless of the distance at which the plant is imaged.

As shown in FIG. 3b, housing 306 may include a shield 308 to prevent water droplets from rain or sprays adhering to the cover of the housing, preventing accumulation of dust and fine debris, and preventing splashes of mud or water from landing on the cover of the housing, all of which may affect the visibility of the CMOS sensor 304. The cover itself may be of high optical transmission (96% or greater), for example optical acrylic or optical glass, and may have scratch-resistant or anti-reflective coatings. Additionally, the cover may be flush with the lens inside the enclosure such that light does not 'leak' into the lens from inside the enclosure. Foam padding may be used to achieve this and provide some damping to prevent damage to the lens or camera from vibrations or shock.

The shield 308 may be transparent to prevent light from LEDs 302 being blocked, or it may be opaque to act as a lens hood depending on the view of the CMOS sensor 304, as required by the application. An opaque cover would also help to shield the vehicle operator from the bright flashes which could be distracting or cause eye discomfort. Additionally, the opaque cover may white, somewhat reflective or may be coated with a reflective material to redirect some light towards the CMOS sensor's field of view. This may additionally improve the image brightness. The image capture device 104 is connected to a power supply via line 309 and to a single-board computer or processor via data line 310.

Figure 22:
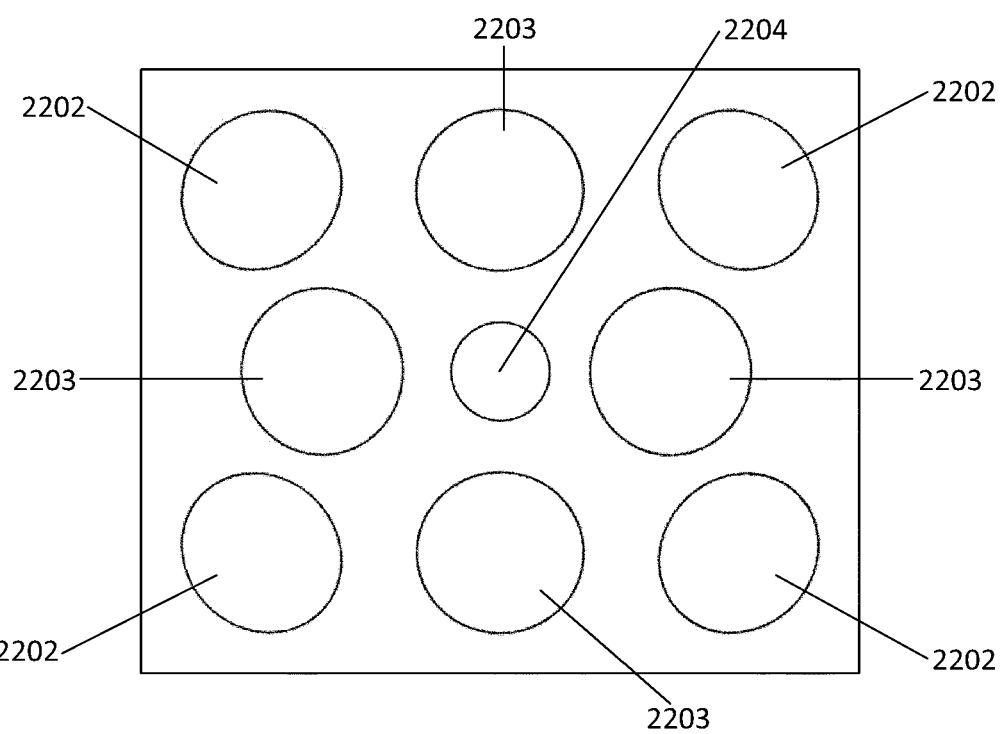
FIG. 22 is a front view of an arrangement of an imaging device.
Figure 23:
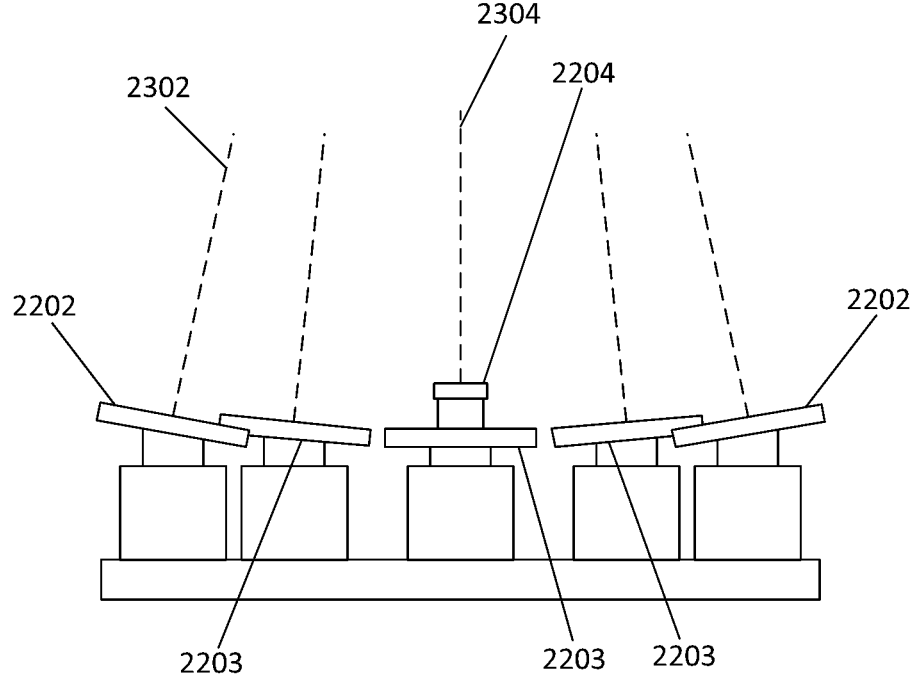
FIG. 23 is a side view of the arrangement of FIG. 22.

FIGS. 22 and 23 show one exemplary arrangement of the illumination sources, which can be the LEDs as discussed above. They are arranged around the imaging device 2204.

As best seen in FIG. 23, the illumination sources are mounted at an angle so that their respective illumination axes 2302 are tilted towards the imaging axis 2304 of the imaging device 2204. Those that are further out 2204 from the imaging device 2204 can be tilted by a greater amount so that the light from all imaging devices converges within the field of view of the imaging device 2204. The angle at which they are mounted may be adjusted to change the distance at which the light converges. For example, the outer lights 2202 are angled at 11 degrees, and the inner ones 2203 are at 6 degrees, based on the subject being 0.3 m to 0.5 m away, and the specific layout of our lights. An option to account for real-time variation in canopy depth and density may use a single or a combination of distance measurement sensors including but not limited to depth cameras, Lidar, infrared or light reflective sensors, or others to adjust the angles of the illumination sources to maintain the convergence point at the average depth of the canopy and maximise light concentration and image homogeneity. Mechanical actuation devices including but not limited to servo motors, linear actuators may be used directly or indirectly through an actuation system to control the angle of the lights.

This arrangement increases the effective light intensity in the imaged area without the need to add extra light sources or increase the applied voltage to the light sources. Because the light is concentrated in the field of view of the imaging device, less light is 'wasted' outside of the field of view.

A laser can also be provided with the imaging device to highlight the field of view of the imaging device. A diffraction grating can be provided to split the laser and shape it to match the field of view of the imaging device. When more than one imaging device is used, the projected laser light from all of the imaging devices can be aligned to align all of the fields of the view of the imaging devices.

The CMOS sensor 304 is a colour sensor, and it uses a global shutter. An optical band-reject filter may be used to block unwanted frequencies of light, for example an infrared cut filter.

Using a colour sensor instead of monochromatic may help to detect a wider range of different pests and diseases. Colour information may also be used to identify other issues such as nutritional deficiencies, water stress, canopy "greenness", canopy density or vigour, leaf-area index, missing vines, estimating fruit ripeness, aid in counting buds/fruit for yield estimation, or aid in counting trunks or posts, depending on the requirements of the application. For example, the image could be segmented based on what's green and what isn't, and calculating the percentage of green to measure canopy density. Counting trunks is useful to track how many vines/plants there are in the crop, as some plants often need to be uprooted because of incurable diseases. Missing vines could also be found using the canopy density method in conjunction with counting trunks. It could also be a basis for leaf-area index (again, finding green areas which happen to be leaf shaped). Counting posts and mapping out their locations is useful as they're often used as landmarks in the vineyard to tell workers where they need to go.

The global shutter prevents any distortions, for example, motion blur, in the images while the vehicle is moving. In a vineyard, for example, tractors will typically go 8 to 12 km/h, and All Terrain Vehicles will go up to 30 km/h.

To reduce the effect of ambient illumination and specular reflection, various approaches may be taken, according to the requirements of the application. First a very low exposure time may be used for the CMOS sensor 304. Depending on the environmental variables, and the sensor used, this may be similar to high speed photography, and in one example the exposure may be between 30-200 us.

Figure 4:
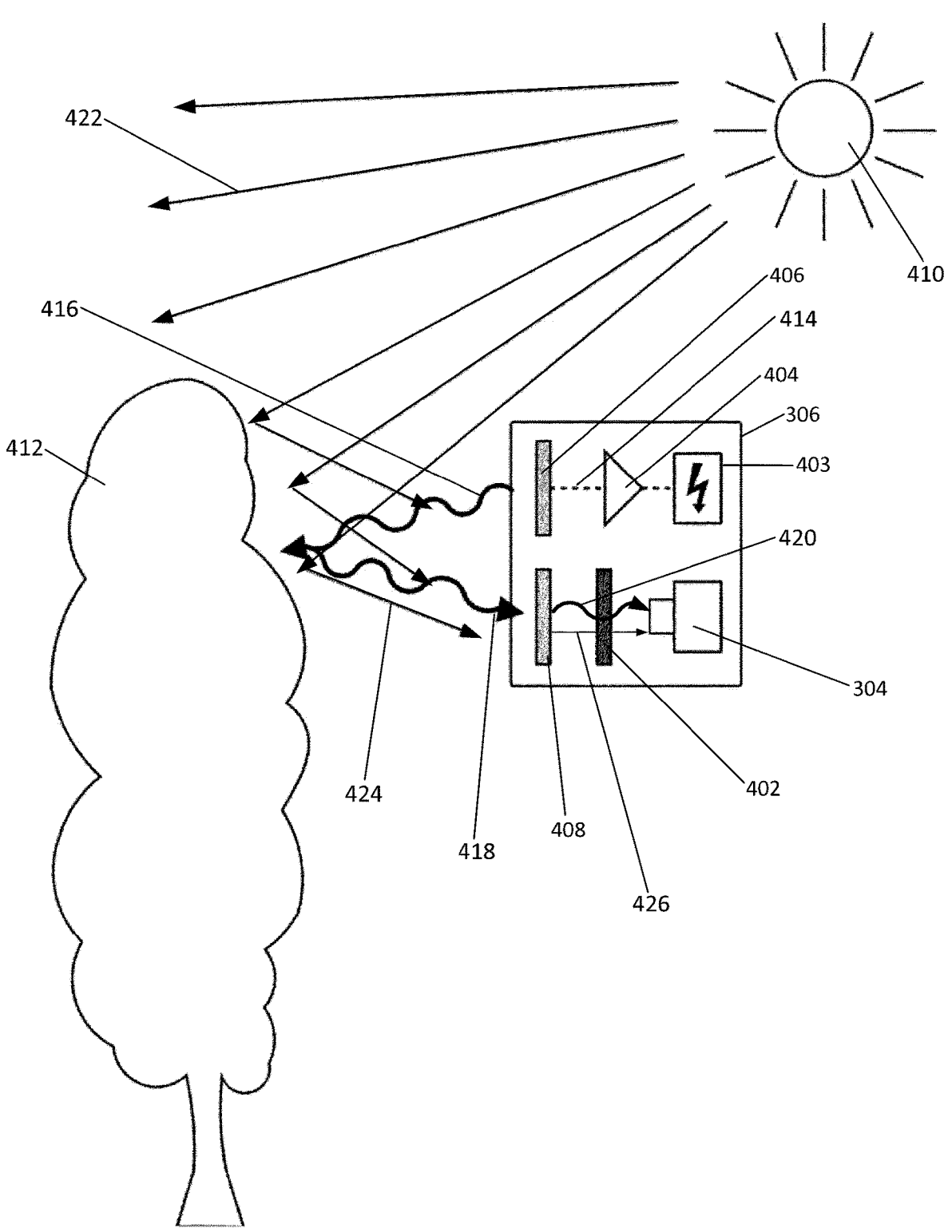
FIG. 4 is a schematic depiction of image capture system according to an example embodiment.

Secondly as shown in FIG. 4, the image capture device 104 may incorporate a neutral density filter 402 in front of the sensor 304 to darken the scene further. The neutral density filter 402 may for example be a single filter or multiple filters stacked on top of each other to produce a collective darkening effect corresponding to an optical density between 0.046 to 3.0. The neutral density filter 402 may be designed to darken the image and affect all colours equally such that the ratios between darkened colours are preserved and the image colour integrity is maintained. The neutral density filter 402 may be designed to also absorb or reflect wavelengths outside the visible spectrum such as infrared or UV light, e.g. below 380 nm or above 740 nm.

Thirdly the lens aperture of the CMOS sensor 304 may be adjusted to darken the scene. For example, the aperture may be adjusted to f/16 between f/8 and f/16, (though beyond f/16 could also make the image even darker) with a focal length of 6 mm to ensure adequate depth of field and that the image is in focus, and (if necessary) to minimise barrel distortion.

Fourthly as shown in FIG. 4 cross polarisation may be used to reduce reflection artefacts from the leaves or other parts of the plant. Reflection artefacts can make it difficult or impossible to image surface features of the plant. While simply imaging the overall shape of fruit or other plant parts may be enough to roughly estimate yield, canopy cover, leaf-area index etc. in some situations, some analyses require analysis of the surface of the plant. For example, pest and disease detection may use segmentation of the image of leaf surfaces to identify blemishes caused by fungal bodies, signs of pests, or pests themselves. Reflections obfuscate these surface features making it unclear or impossible to view them.

In the example of FIG. 4, a plant 412 is being imaged during the day, with ambient light 422 being produced by the sun 410. The illumination source produces illuminating light 414 for illuminating the plant 412. The illuminating light is passed through a first polarising filter 406 to produce polarised illuminating light 416. The polarised illuminating light is reflected off the plant 412 to produce reflected polarised illuminating light 418. The reflected polarised illuminating light 418 is passed through a second polarising filter 408 that has a polarisation axis transverse to that of the first polarising filter 406. This cross-polarises the light 418 to produce cross-polarised reflected illuminating light 420 with significantly reduced specular reflections. This cross-polarised light 420 is captured by the image capture device for imaging the plant 412.

Ambient light 422 is also reflected from the plant 412 to produce reflected ambient light 424. This is inevitable in a situation where the imaged plant cannot be shaded from ambient light, which is typically the case in the field. The reflected ambient light 424 will also pass through the second polarising filter 408 to produce polarised reflected ambient light 426 which will also enter the image capture device along with the cross-polarised light 420.

The illumination source produces high-intensity light so that the cross-polarised light 420 received by the imaging device is of a greater intensity than the polarised reflected ambient light 426. This reduces the presence of reflections from the ambient light (which is not cross-polarised) in the captured image. The illumination source can be bright enough that the intensity of the cross-polarised light is 2, 5, 10 or more than 10 times greater than that of the polarised reflected ambient light 426. In the case that ambient light is provided by the sun 410, this means that the illumination source's light needs to overpower the sun's light in the captured image by this amount. As discussed below, this can be achieved using overdriven LEDs, although other suitable illumination sources such as halogen bulbs or high intensity sources could be used in some applications.

Using a polarised active illumination source to illuminate the plant avoids the need to polarise ambient light such as sunlight. This makes the system more convenient and suitable for use in the field because light from a lighting device like an LED can easily be polarised by a small polariser carried around with the device, whereas polarising ambient light requires large and unwieldy polarisers than are not easily transportable. Active lighting also minimises shadows in the image and more evenly illuminates the plant to expose the features and colours of the plant parts such as leaves, fruit and stems-particularly in outdoor conditions.

As noted above, using high-intensity illumination sources that overpower ambient light sources avoids the need to shade the plant from ambient light during imaging. When the illumination sources are sufficiently intense to overpower the sun, this enables imaging to be performed during the day on unshaded plants. This is much more convenient than only imaging at night or in other low-light conditions. The greater the degree to which the illumination source overpowers the sun, the less the reflections from the sunlight affect the captured image.

The system can be used to analyse the surface of plants outdoors in a range of conditions, which makes it much more suitable for large scale application in the field. Improved surface imaging and analysis improves the ability to detect or segment bunches of fruit, shoots, berries and buds to improve yield estimates. It also allows for the detection of pests and diseases, nutritional deficiencies, water stress, chemical residues (which indicate spray efficiency), fruit colour (which indicates ripeness and can be used to sort fruit for different markets according to its colour profile, for example), leaf-area index, canopy density, posts (this help growers identify which bay and row an infection is in, and which may be used instead of or in addition to GNSS location), broken posts which need to be replaced, plant trunks (to keep track of missing plants), and untreated cuts. When the plants are pruned, a brightly coloured seal may be painted onto the open cuts to prevent diseases from infecting the plant. If so, using a colour imaging sensor also makes it easy to spot if a cut has been treated or not.

Loss of light through a polariser should be taken into account when designing the system. A dichroic linear polarising film, for example, will typically only transmit up to about 42% of incident light. This means that with two of these polarisers, the total transmitted light will be up to about 0.42*0.42=0.18 or 1/5.6. The illumination source should therefore be at least 5.6 times as intense as it would otherwise need to be without the polarisers.

Each of the 8 LEDs 302 may include a white LED 403, a LED lens 404 in front of the LED 403, and a 0° polarising filter 406 in front of the lens 404. The CMOS sensor 304 may include a 90° polarising filter 408 mounted in front of a neutral density filter 402. The polarisers need not be at exactly 90° to each other to be effective, although they will be most effective when closest to 90° to each other.

The LED lens mounts, LED lenses, heatsinks may all be mounted to a PCB board with a hole in the centre for the CMOS sensor. The PCB may be fixed to the housing 306 with screws and may take up most of the space in the housing 306. A water and dust resistance rating of IP64 for the housing will be sufficient to resist dust, 10° rain, humidity, or sprays. The housing 306 may include a waterproof vent to allow humidity to escape and prevent condensation, such as a GORE™ Vent. The housing 306 may be UV stabilised, and not deform when out in the sun from the heat and UV.

The LED lens 404 may for example be a wide beam lens to spread the light from the LEDs 403.

The 0° polarising filter 406 may for example be a linear absorptive polariser.

The 90° polarising filter 408 may for example be a linear absorptive polariser identical to and mounted perpendicularly to polarising filter 406.

Figure 18:
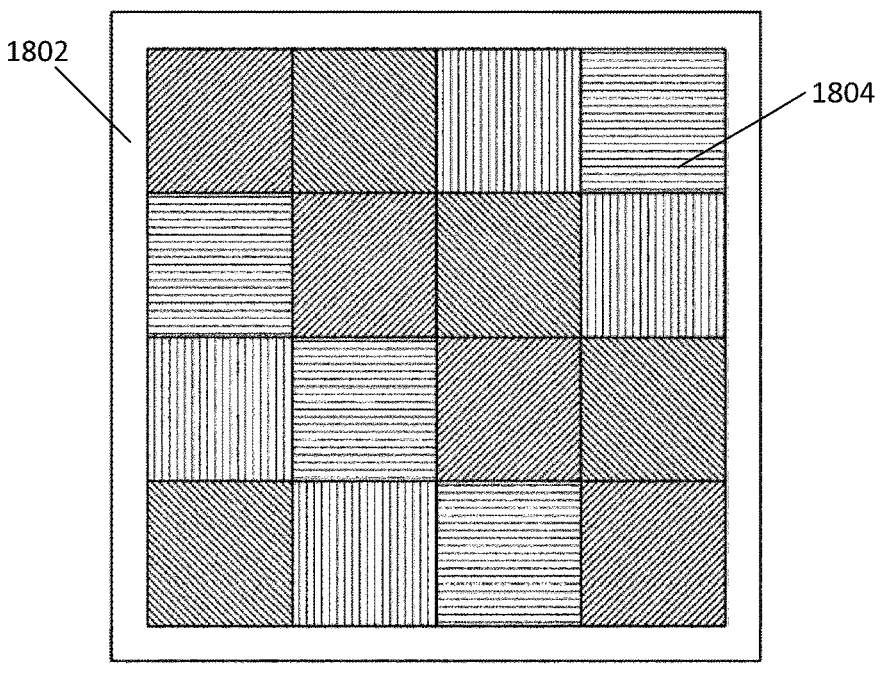
FIG. 18 is a front view of an imaging device according to one example embodiment.

The system can also include several second polarisers for polarising the light reflected from the plant. These second polarisers have different polarisation axes to provide several different views of the plant. Simple cross light polarisation with only one polariser for the reflected light can sometimes miss detail that is visible at certain angles, fungal disease fruiting bodies for example. The different polariser angles can allow for images to be taken with full, partial and no (or minimal) specular reflections to improve detection capability. The second polarisers can be used with a single image sensor, or each polariser can provide filtering to its own image sensor. FIG. 18 shows one such arrangement, with 16 different polarisers 1804 overlaying an image sensor 1802. The polarisers have polarisations axes of 0°, 45°, 90° and 135°. An exemplary device with several polarisers on a single image sensor is the Sony IMX250MZR/MYR polarisation image sensor.

A depth sensor could be used for the purpose of calculating and calibrating size of detections. e.g. Bunch size, fruit size etc. for yield and forecasting.

The illumination device can be one or more LEDs, in this case white LEDs 403. Fifthly the white LEDs 403 may be strobed. Depending on the LEDs used, a strobe mode is possible where the nominal or average input rating eg: 110 W may be achieved by only powering the LED for a very short period in each duty cycle, but to a much higher level without damaging the LED. This allows the lumen output of a relatively cheap LED array to be significantly higher than the sun (>100,000 lux). This in turn may obviate the need for a sun shield, without a commercially infeasible illumination cost.

The white LED 403 may for example be a chip-on-board LED that is high-power (depending on the application a different cost vs. size vs. overall output may be desirable), with a high colour rendering index (CRI), for example 80 CRI, and cool colour temperature, for example 5700K, to preserve real-life colours in captured images. The increase in drive current during on time should be designed up to a maximum based on the rated maximum current increased proportionally to the reduction in duty cycle.

For example, the current could theoretically be increased by up to 50 times the rated current for an increase of up to 100 times the rated electrical power. If the nominal LED voltage is 72V (relatively large high-power LED e.g. Cree™ CMA3090R), during strobe mode, with a duty cycle of 0.08%, the drive voltage could be increased by 3 times the rated voltage to achieve such an increase in current without damage. In other words, empirical testing will be required for a particular design, as with very small duty cycles, the practical maximum current during on time, will be less than a proportional value due to other considerations. These may include high frequency effects and the package thermal time constant in comparison to the pulse width-if the heat generated during the pulse is not able to be dissipated through the package quickly enough, the LED will fail. As the thermal time constant of the LED package increases as the device gets larger, smaller devices can be driven closer to the theoretical maximum, but a higher number of lower power (smaller) devices may take up more real estate and require a bigger housing, or cost more in total per lumen than larger devices.

So, if the strobe frequency was 5 Hz (period of 200 ms) then a pulse width of 100 us would be possible. This would equate to a practical frame rate of 5 frames per second (FPS) and exposure time of 100 us on the CMOS sensor to illuminate the subject area. In practice the exposure time could be specified first in the design process, according to the maximum design speed of the vehicle carrying the system to avoid blurring.

The LED bond wires and associated power supply must also be able to supply and support the massively increased current, albeit for a 0.08% duty cycle. This may require a low inductance circuit and may also require magnetic shielding to reduce EMI to a regulated level.

Overdriven LEDs can warm up more quickly than LEDs driven at or below a rated voltage. If the heat is not adequately dissipated, the junction temperature of the diodes can eventually get too hot and the bond wires will melt, resulting in the failure of the LED. One way to deal with this is to only allow the LED to emit light for short durations.

An active cooling method such as a refrigeration system or Peltier cooler can be used to cool the LED significantly below ambient temperature to create a 'temperature buffer'. This is shown in the FIGS. 19 and 20 discussed below whereby lowering the starting temperature allows the LED to emit light for longer before failure. More time in which the LED is emitting light results in higher overall light output.

Alternatively, if the LED is being flashed for a set duration—200 us for example—the supercooled LED will have a lower peak temperature than its ambient counterpart. This puts less stress on the circuit over time and may increase the LED's longevity.

Figure 19:
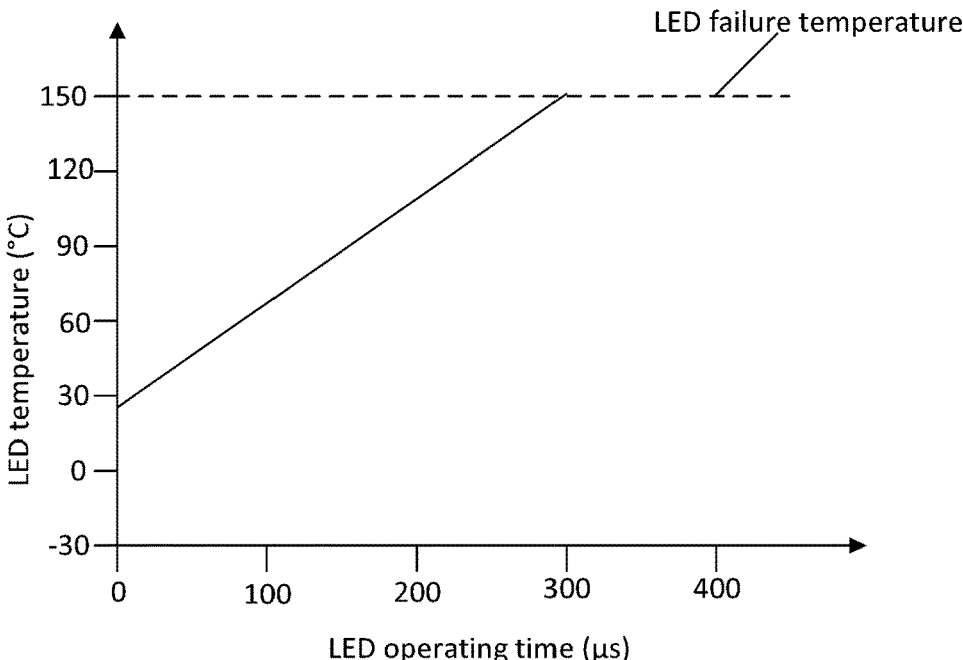
FIG. 19 is a graph of operation of a non-cooled LED.
Figure 20:
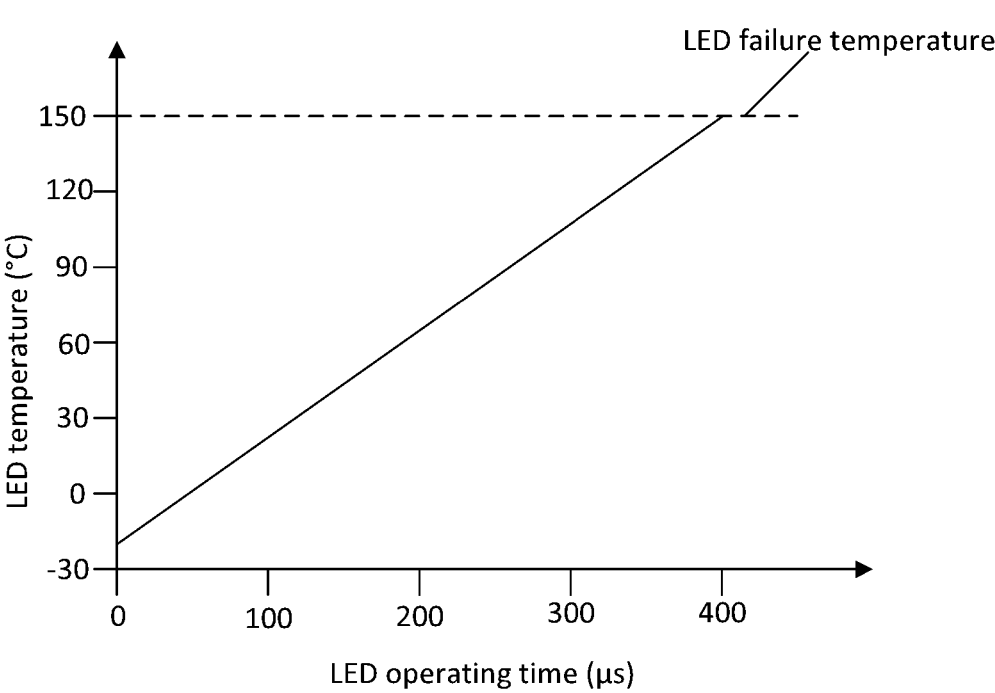
FIG. 20 is a graph of operation of a cooled LED.
Figure 21:
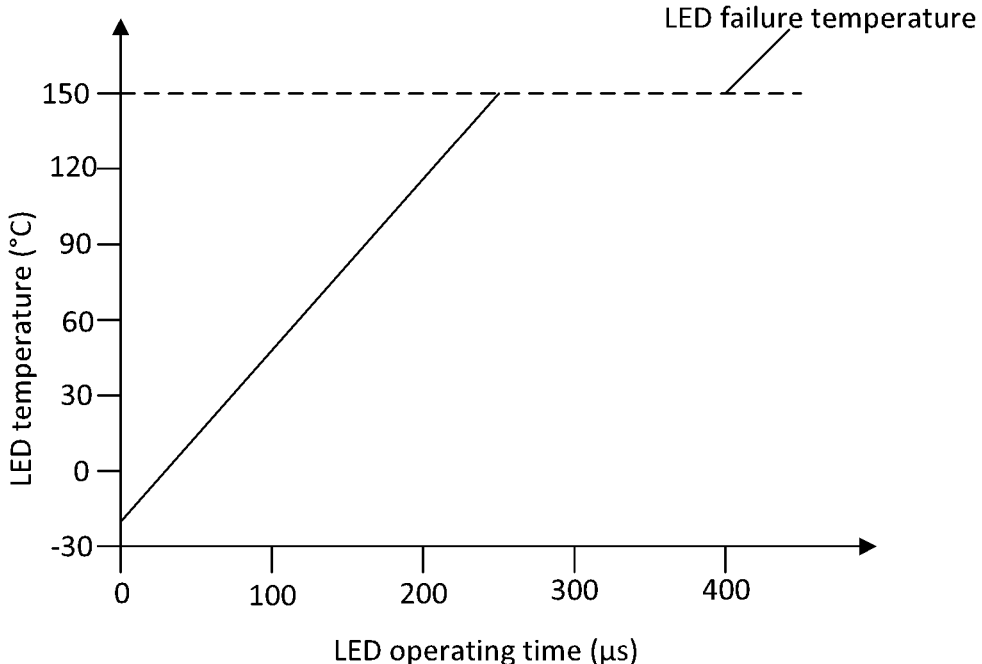
FIG. 21 is another graph of operation of a cooled LED.

Examples of LED operational characteristics are shown in FIGS. 19 to 21. In these examples, a Cree® XLamp® LED is considered, where the maximum junction temperature is typically 150° C., at which point the LED can permanently fail.

In FIG. 19, a non-cooled LED has a voltage 1.5 times greater than its rated voltage applied to it, at a room temperature of 25° C. The temperature of the LED rises until it reaches the failure junction temperature of 150° C. after 300 us.

In FIG. 20, an LED is initially cooled to −20° C., then a voltage 1.5 times greater than its rated voltage is applied. Assuming a similar gradient of temperature increase to the non-cooled LED, the temperature will rise for over 400 us without. reaching the failure temperature of 150° C. This shows that the cooled LED can be overdriven by the same factor as a non-cooled one for a longer time than the non-cooled one without failing.

In FIG. 21, an LED is initially cooled to −20° C. then a voltage 3 times greater than its rated voltage is applied. The temperature rises more steeply than in the previous examples (FIGS. 19 and 20) and reaches the failure temperature of 1505° C. in 250 us. Despite the time to failure being reduced slightly compared to the other examples, the light output (both instantaneous and integrated over the operation cycle) will be increased significantly when the applied voltage is increased by a factor of 3. This shows that greater light output can be achieved by cooling the LED.

Additionally, an operational 'sweet spot' can be found by balancing increased light output (due to higher overdriving ratio) with increased length of operating cycles and longevity (due to lower peak voltages). For a cooled LED, the light output and/or operating cycle length and longevity can be greater at this 'sweet spot' than they would be for a non-cooled LED.

Gain determines the sensitivity of the sensor; however, the higher the gain, the greater the amount of noise in the image, and this may introduce artefacts in the image that can affect detection of issues. To keep noise to a minimum, lower values are preferred. A gain of 0 to 10 may be sufficient.

While white LEDs and a colour CMOS sensor have been described above, in different applications, other wavelengths or bands may be used, such as invisible bands, infrared, ultra violet, other EM technologies such as radar or lidar, or mechanical waves such as ultra-sonic or sonar.

The image capture devices 104, 106, 108 may be configured according to the requirements of the application. In FIG. 1 the lower image capture devices 108 may be directed at the fruit 114, the mid image capture devices 106 may be directed at the mid canopy 116, and the upper image capture devices 104 may be directed at the upper canopy 118.

Figure 5:
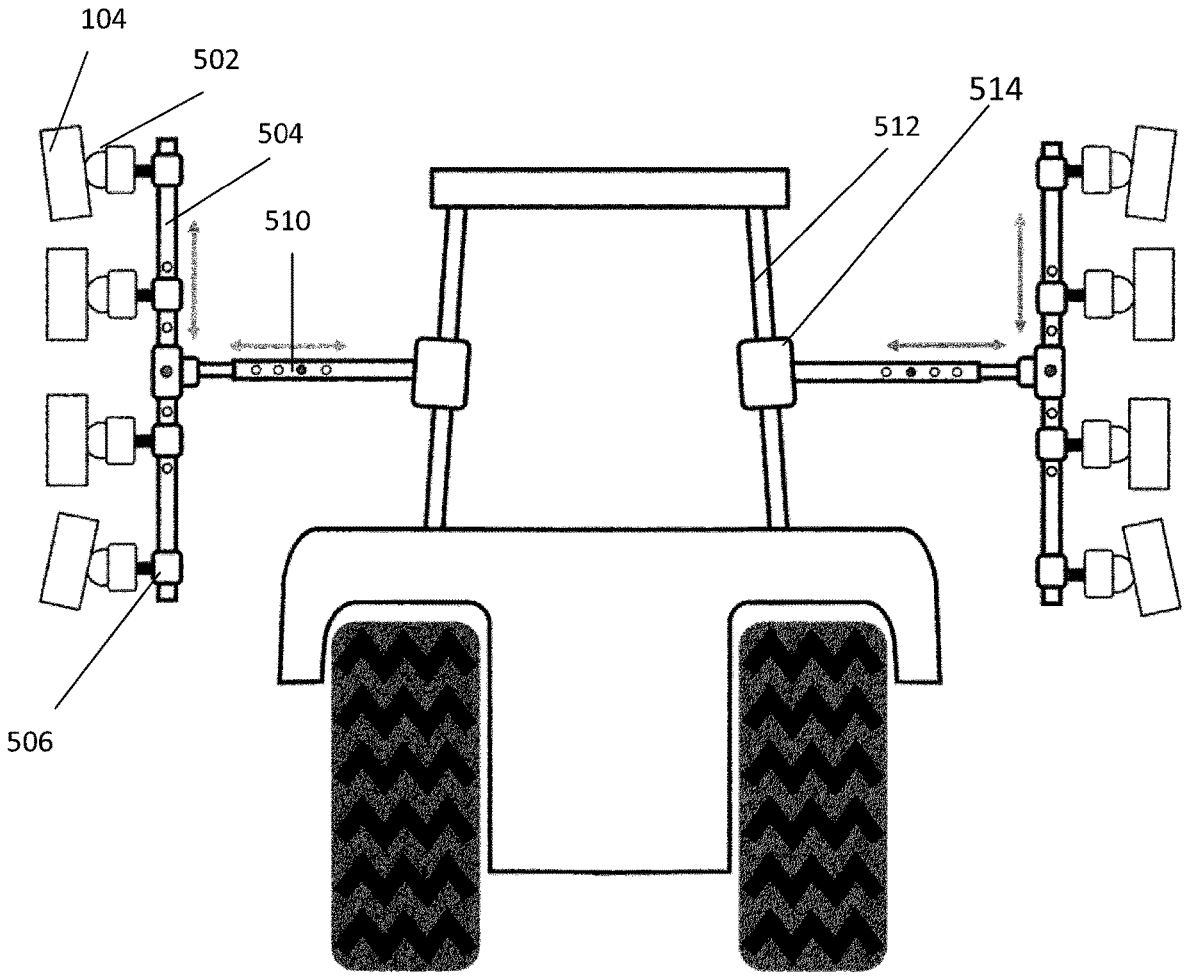
FIG. 5 is a rear view of a tractor showing an alternate capture device connection structure.

Each image capture device 104 may be mounted as shown in FIG. 5 to achieve the desired camera locations and orientations. The housing 306 includes a ball and socket attachment 502 to the back face which allows orientation adjustment and connects to a generally downward facing shaft 504. Shaft 504 vertically slides within a clamp 506 allowing vertical adjustment. Shaft 504 is attached to a generally horizontal telescoping shaft 510 which is mounted to the tractor frame 512 allowing horizontal adjustment.

Also shown in FIG. 5 are mounts 514 for mounting the imaging system to the vehicle. The mounts 514 can be suction cups. These are cheap and easy to install on a vehicle such as a tractor. They also make the system highly adaptable because they can be attached to any smooth, flat surfaces like windows, plastic walls or painted metal. This may also help install imaging devices in the optimal position or orientation by translating or rotating the suction cup mount. Additionally, the suction cup will safely release from the vehicle if the mounted system hits an obstacle without damaging the mounting arrangement or imaging system—a backup catch may be in the form of a cable or tie, where one end secured to the device and the other to some point on the tractor such as around the door handle or wing mirror. In the event that the suction cup fails, the device will be caught by the backup tie rather than impacting the ground and potentially being run over by the vehicle. Suction cups also provide some vibration damping between the vehicle and the imaging system. Suction cups can also be used to mount other equipment, such as a blower, to the vehicle.

Blower

At different stages of the growth cycle the fruit or produce may be exposed or it may be covered by foliage. Equally, disease may occur on the undersides of the foliage. For example, powdery mildew and downy mildew exhibit similar symptoms in the early stages; however, powdery mildew exhibits different symptoms on top of the leaf while downy mildew exhibits different symptoms on the underside of the leaf. Mealybug, a devastating pest, lives under the leaves as well. Depending on the application it may be desirable to displace the foliage to capture images of the fruit or produce and/or the underside of the foliage.

The blower 110 is shown in more detail in FIGS. 6a to 6d. An air pulse arising from below the leaves combined with a co-ordinated camera trigger is used to capture the underside of leaves. Air is likely to be pulsed in short periods as to avoid missing the overside of the leaf during normal collection. To achieve this the blower 110 will be mounted slightly ahead of the camera. The blower will be pulsed so the camera can capture images of the tops and bottom of the leaves (not necessarily of the exact same leaves, but close). In FIG. 2 Blower 110 is shown mounted to shaft 504 through two forwardly extending poles 120 that are perpendicular to, and may slide over, each other. Subsequently the poles are attached to a horizontal shaft and ball socket 122 to the nozzle 124.

Figure 6A:
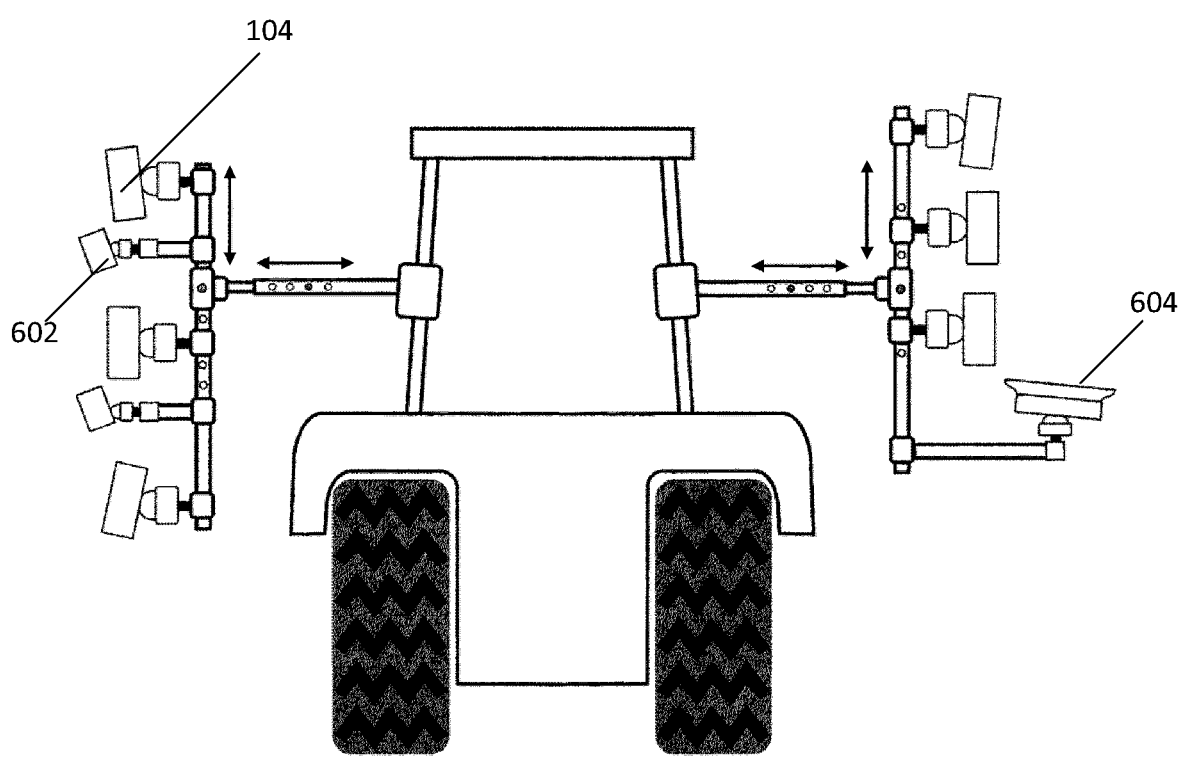
FIG. 6a is a rear view of the tractor in FIG. 2 with the addition of alternative leaf blowers.

The blower may take different forms depending on the requirements of the application. For example, as shown in FIG. 6a, each image capture device 104, may have a corresponding individual nozzle 602 (further examples shown in FIGS. 6b and 6c), or a single nozzle 604 (example in FIG. 6d) may be placed on the bottom to blow the leaves upward, or near the top in reverse to suction the leaves up. FIG. 6c also shows the hose 605 connecting the blower to a source of pressurised gas such as an air compressor.

Increasing turbulence can help to agitate the leaves or other plant parts so that more of their surface, including the underside, can be imaged.

One option is to take a photo of the canopy undisturbed, then generate a pulse of air and time it so that when the pulse disturbs the region of interest the second photo is taken, repeat for each scene. Timing the second photo will often require trial and error so an AI based solution may suit.

A second option is to use two cameras per scene, with some displacement (~30 cm+). One camera captures undisturbed photos. The second camera has the blower attached to it and constantly captures disturbed canopy photos. Use cm-level geo-tagging to merge the results in post.

A third option is to use a single camera with a single powerful blower with a turbulence grid. Capture and analyse multiple photos per scene, Use cm-level geo-tagging and AI or IMU tracking to merge the results in post. This assumes that most things are exposed by the blower for each scene.

Figure 6B:
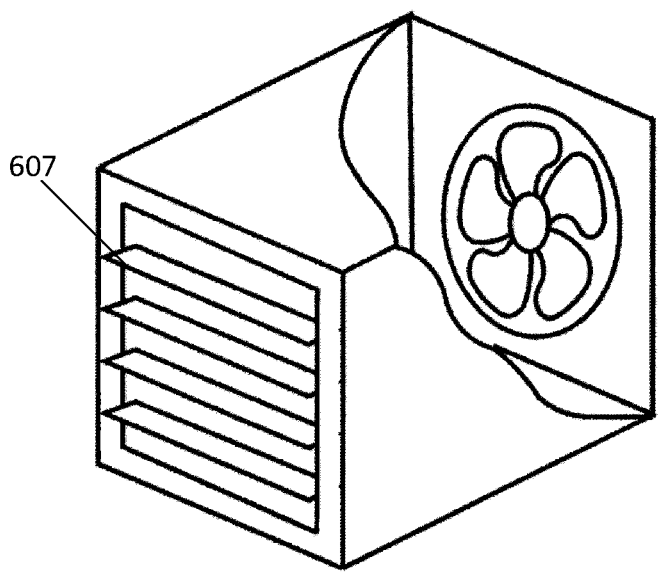
Figure 6C:
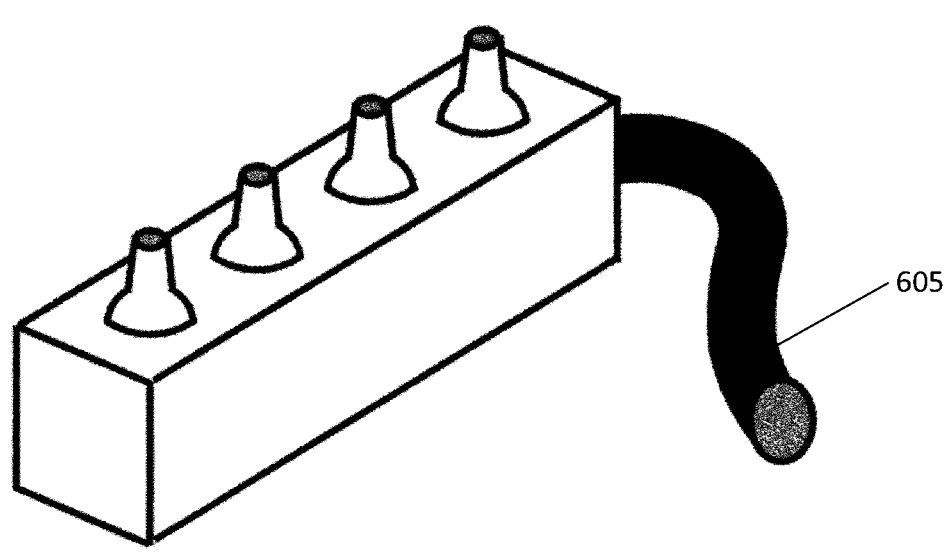
Figure 6D:
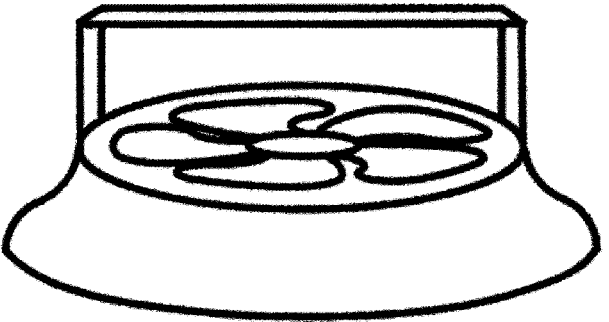

The blower of FIG. 6b has vanes 607 for directing airflow from the blower. The vanes 607 can be tilted in different directions to move the airflow around and effectively increase turbulence of the airflow on the leaves. The blower of FIG. 6e has a grid of slats 606 running in different directions to increase turbulence of the airflow. Alternatively or additionally, the air supply to the blower can be pulsed to increase turbulence.

One exemplary blower 2500 is shown in FIGS. 25-28. The blower 2500 includes a RAM mount assembly with a fan head 2502, mounting arm 2504, suction cups 2506 and a ball joint for attachment to the vehicle and a heat sink assembly 2508. An automotive regulator and boost converter are mounted with a heat sink assembly 2508 and dissipate heat into the blower's air flow using cooling fins of the heat sink. An adjustment knob 2510 is also provided to tighten or loosen the mounting arm 2504 from the ball joints on either end. The mounting arm on a RAM mount is in two halves (length-wise) and the knob in the middle has a screw or bolt which can then bring the two halves together and tighten the grip on the ball.

Figure 29:
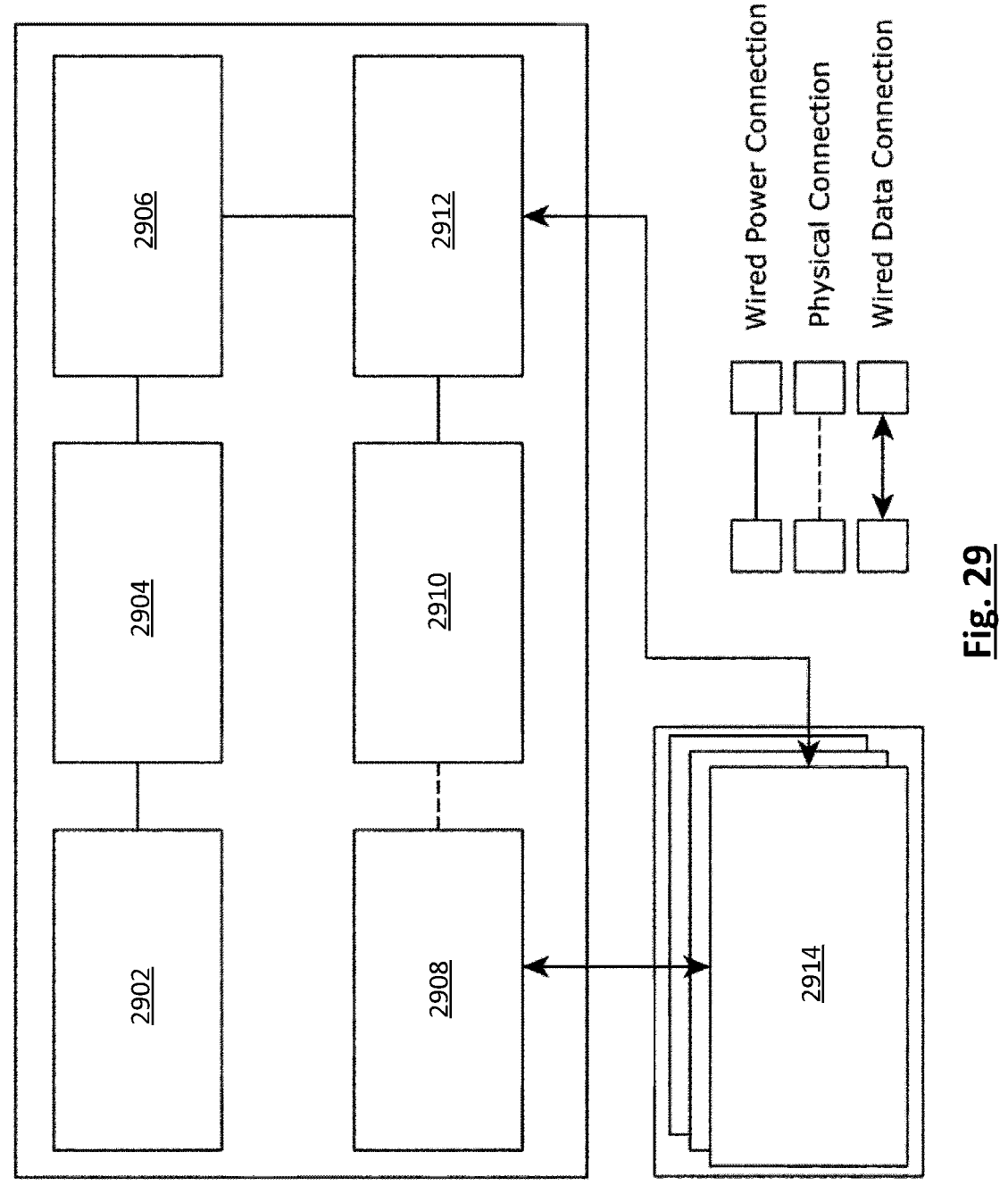
FIG. 29 is a block diagram of the leaf blower hardware according to one example embodiment.

Exemplary blower hardware is shown in FIG. 29. This includes 12V vehicle battery 2902, automotive regulator 2904, boost converter 2906 for outputting 48V, tachometer 2908, fan 2910, pulse-width modulation (PWM) controller 2914 and single-board computer(s) 2914.

Figure 30:
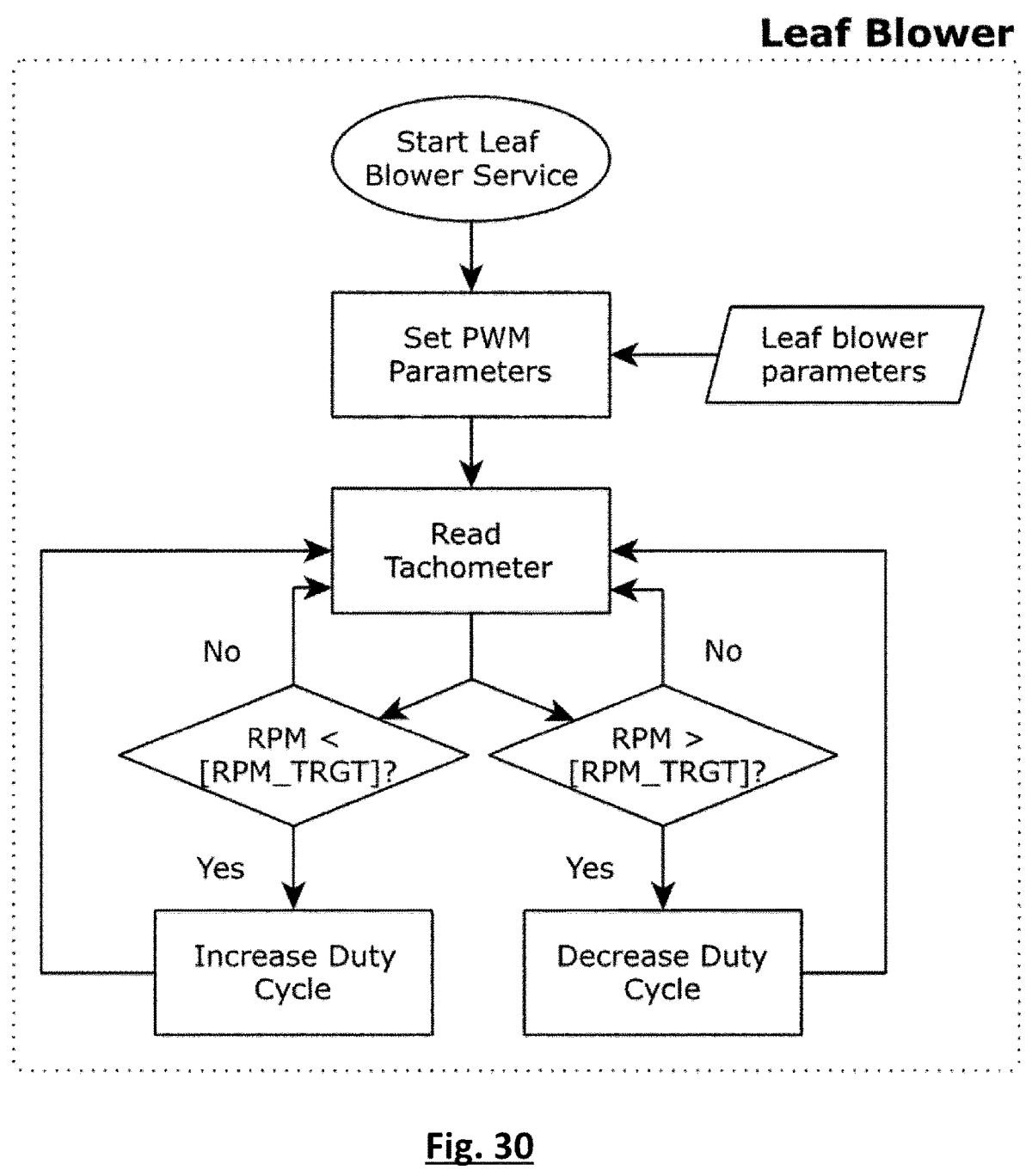

FIG. 30 is a flow chart depicting an exemplary leaf blower speed control algorithm used to program the single-board computer 2914. It uses a closed feedback loop to operate the fan at a fixed Target RPM level. Alternatively it may be pulsed according to a predetermined strategy.

Sprayer

Figures 6E, 7:
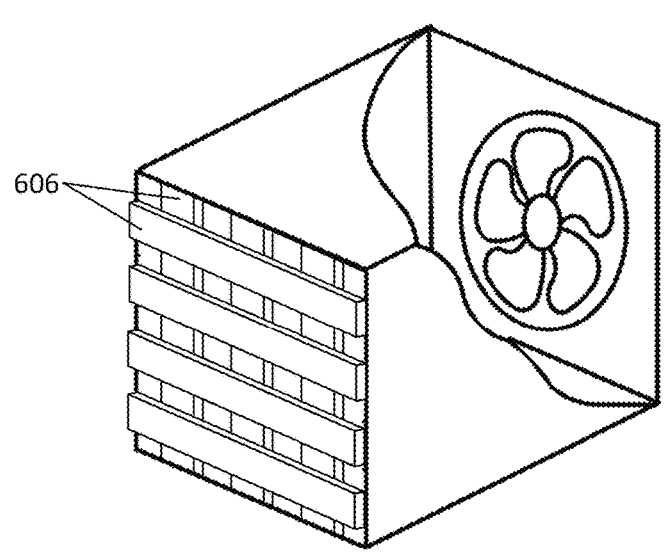

The sprayer 112 is shown in more detail in FIG. 7. Typically spraying in vineyards includes regular spraying of protectant, with occasional spraying of eradicant depending on prevalence of disease or pests. In this case a main tank 702 of protectant, which may be sprayed on the entire crop, can be combined with targeted spraying of specific eradicant, depending on the detection of respective types of disease or pests.

Small reservoirs 704, 706, 708 of concentrated "eradicant" (for each respective disease or pest) may be fed into the main sprayer line 710 (which is usually a common feature across most commercial sprayers), or via a mixing chamber 712. This results in eradicant being sprayed across the canopy over its entire height. Depending on the application requirement, a "diverter" may be used, so that eradicant is sprayed from certain nozzles (via their respective feed lines) of the commercial sprayer based on which camera registers a detection event. In other words, the application of spray to a detection location could either be 2D with the addition of camera height information. Alternatively, the detection location may be specific to a particular part of the plant, foliage or fruit, and directed application of spray or choice of spray may depend on that detection location and/or the type of disease or pest detected.

There may be a detection controller 714 that determines the location of disease and/or pests. The detection controller 714 may emit a control signal(s) to a sprayer controller 716 associated with the sprayer 112 or an appropriate interface. Alternatively, if the sprayer 112 is integrated with the illumination source, multiple image capture devices 104, 106, 108 and/or blower, then a single controller may be employed. The control signal(s) may do the following:

Turning certain nozzles on/off and/or adjusting speed of the fans.

Actuating independent motorised pumps in the smaller reservoir(s) to feed an appropriate amount of treatment chemical(s) into the main reservoir line or mixing chamber.

Actuating independent motorised pumps in the smaller reservoir(s) to feed an appropriate amount of treatment chemical(s) into individual nozzle/fan lines for extremely targeted spraying.

Synchronising the spraying/pumping actions with the detection system.

The exact implementation may depend on individual growers' current arrangements; some growers may already have a main-secondary reservoir arrangement, thus the auto sprayer may interact with the existing spray controller. Other growers may not have such an arrangement, and retrofitting one or more secondary reservoirs to their existing sprayers may be required.

The controller 714 may orchestrate the different actuations in order to synchronise the illumination, air pulse, capture, and spraying. Additionally, location data may be stored as the system 100 travels through the field, including GPS, acceleration, and/or orientation. This data may be used to program a buffer zone of any size (within the horizontal distance from the camera to the sprayer nozzles) for the sprayer, for example, the sprayer may be actuated to spray for 1.5 metres horizontally on either side of the infection site.

Avoiding a covering to block the sun means that crops that cannot be covered in a practical manner can be scanned. To achieve the same effect (over-powering or removing the effects of the sun in the image), the tall crop would need to be sufficiently covered on all sides to block out the sun. This would require a large tent-like structure, with flexible openings for the canopy to pass through. A camera and lights may be placed under the cover to capture images. The issues likely to be encountered with this approach are:

The flexible openings on the tent may break off or damage soft fruits.

Figure 10:
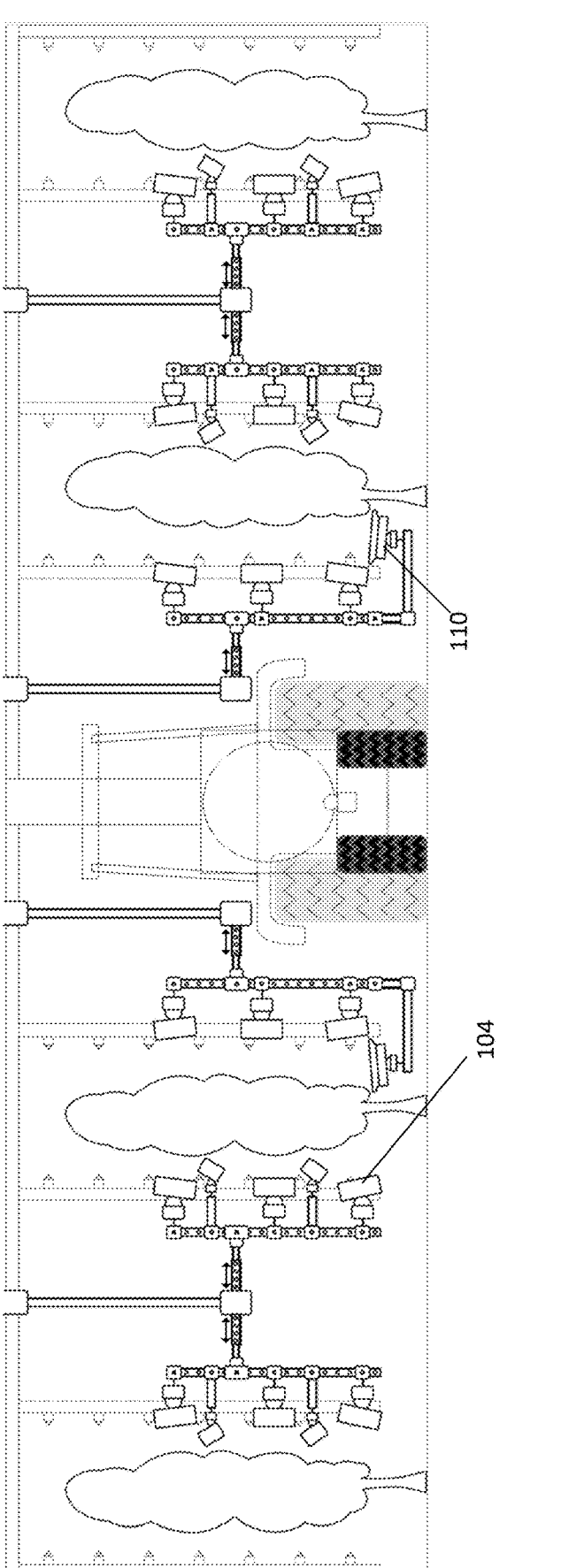
FIG. 10 is a front view of the tractor shown in FIG. 2, with an automated spraying system spanning multiple rows.
Figure 11:
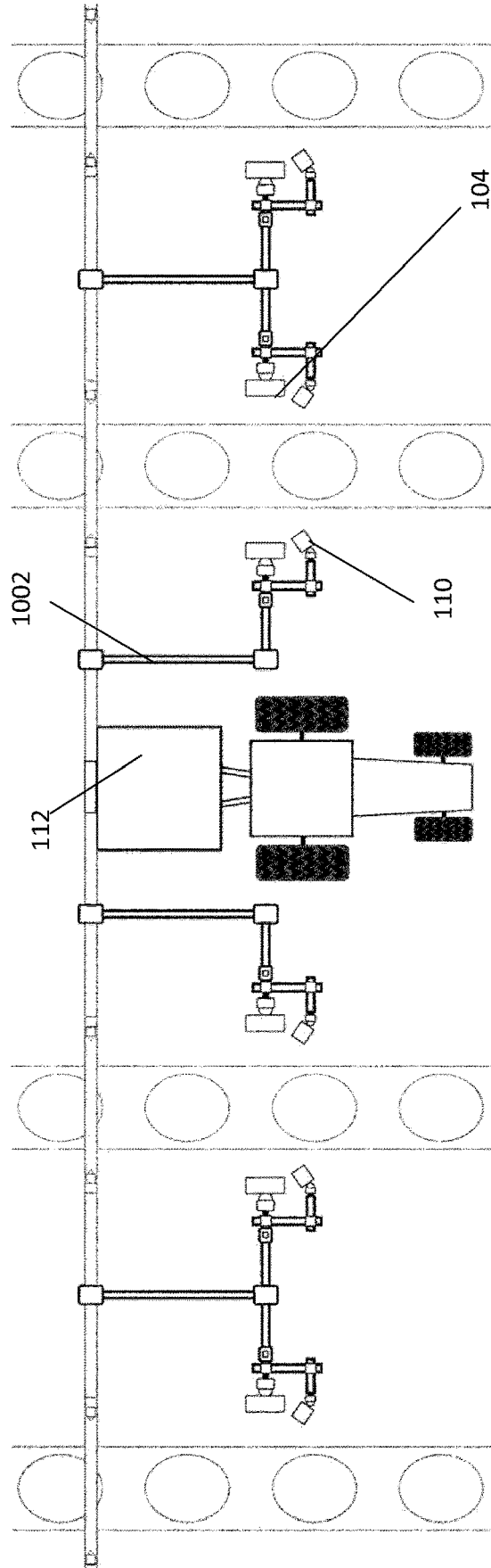
FIG. 11 is a plan view of the tractor in FIG. 10.
Figure 12A:
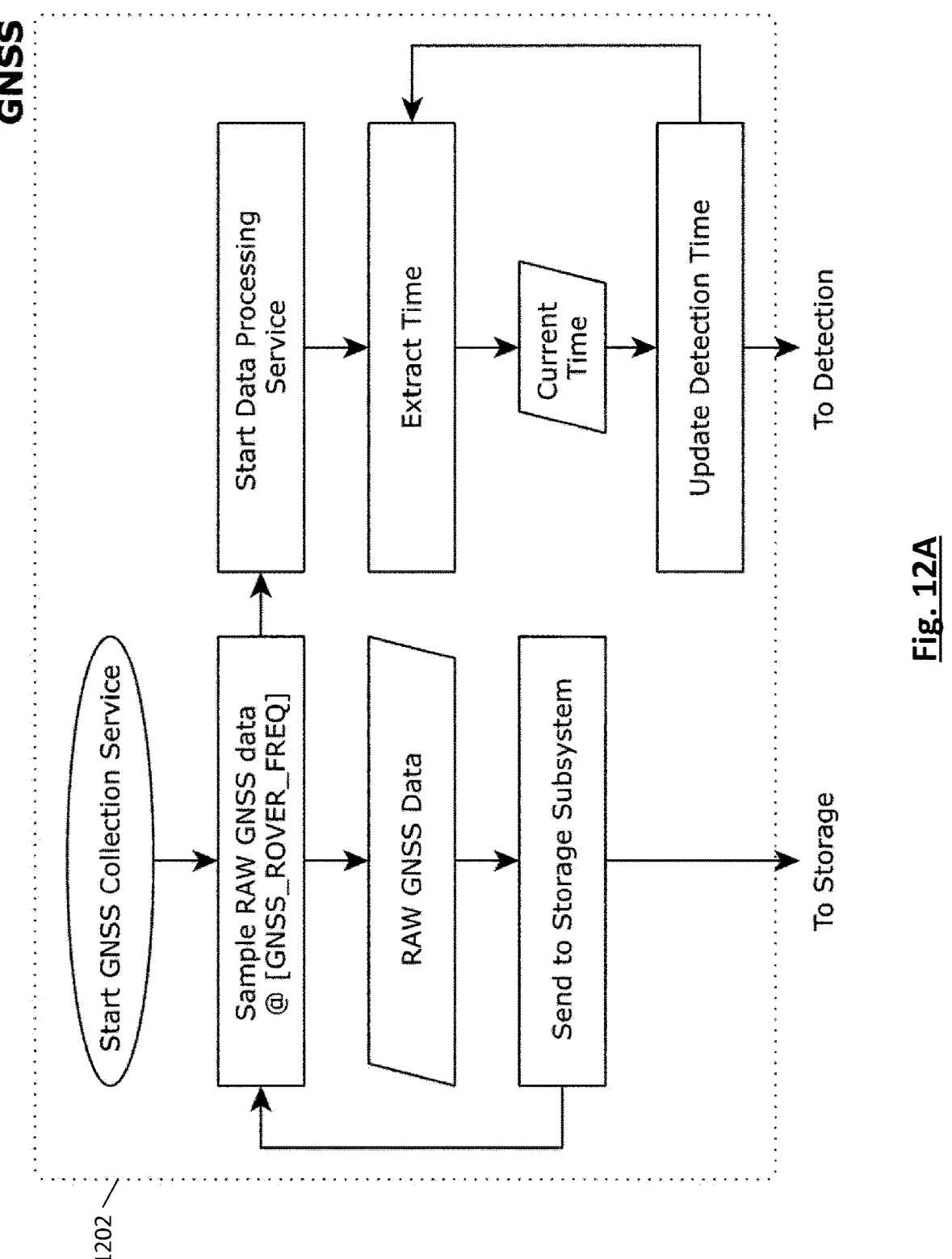
FIGS. 12A to 12G are a flowchart of the software processes executed in the detection controller to handle real-time detection and data storage for later viewing.
Figure 12B:
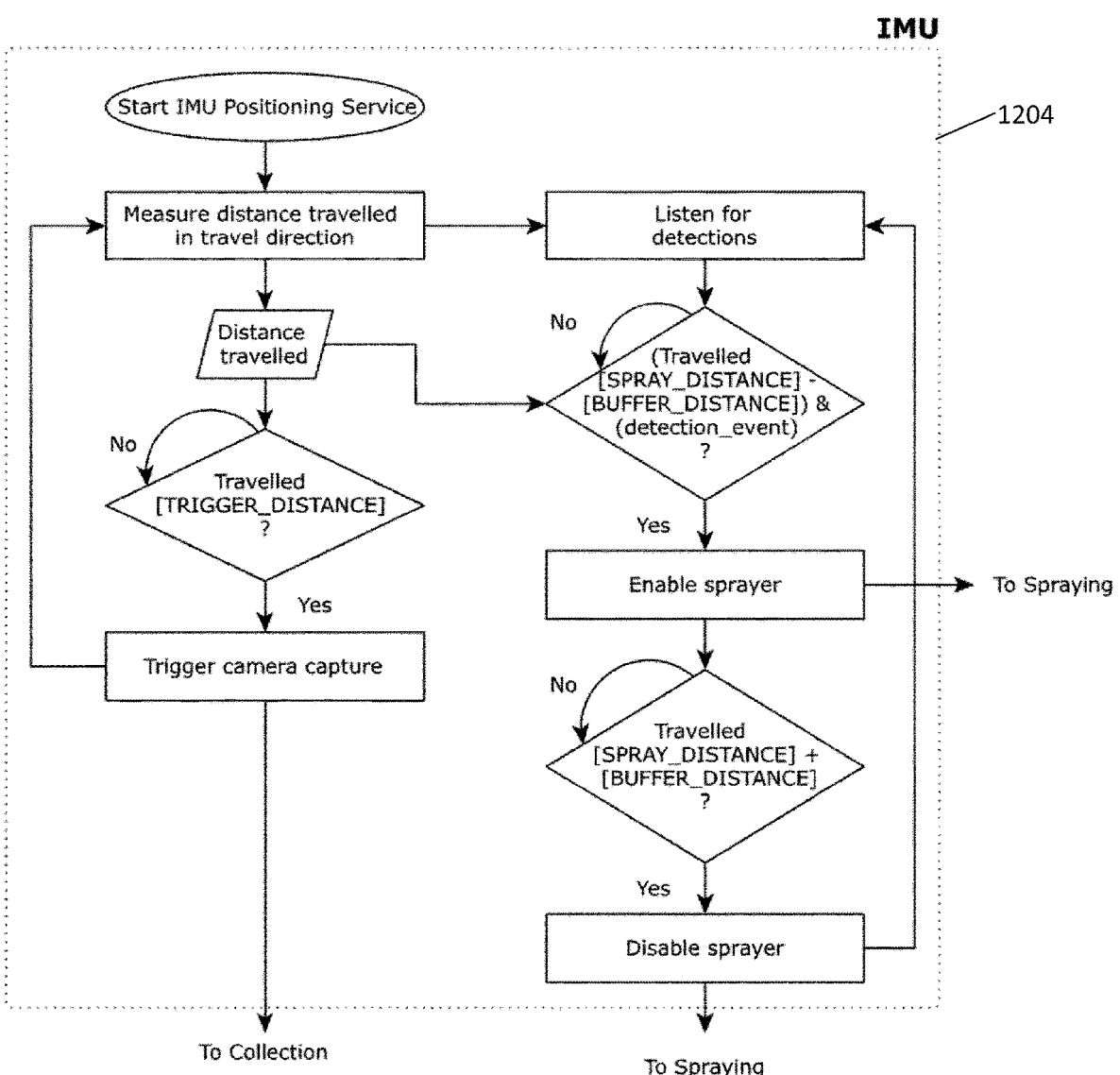
Figure 12C:
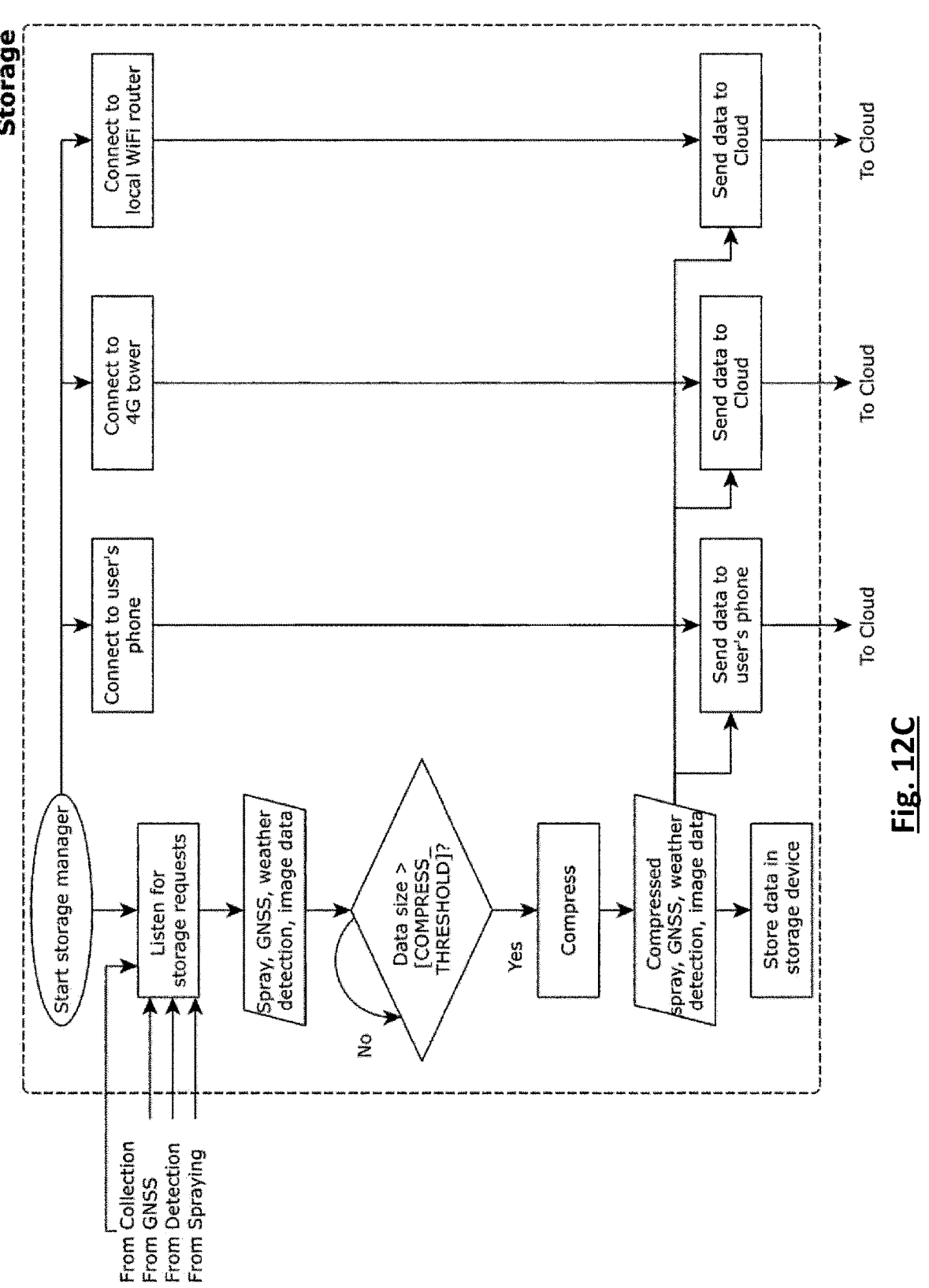
Figure 12D:
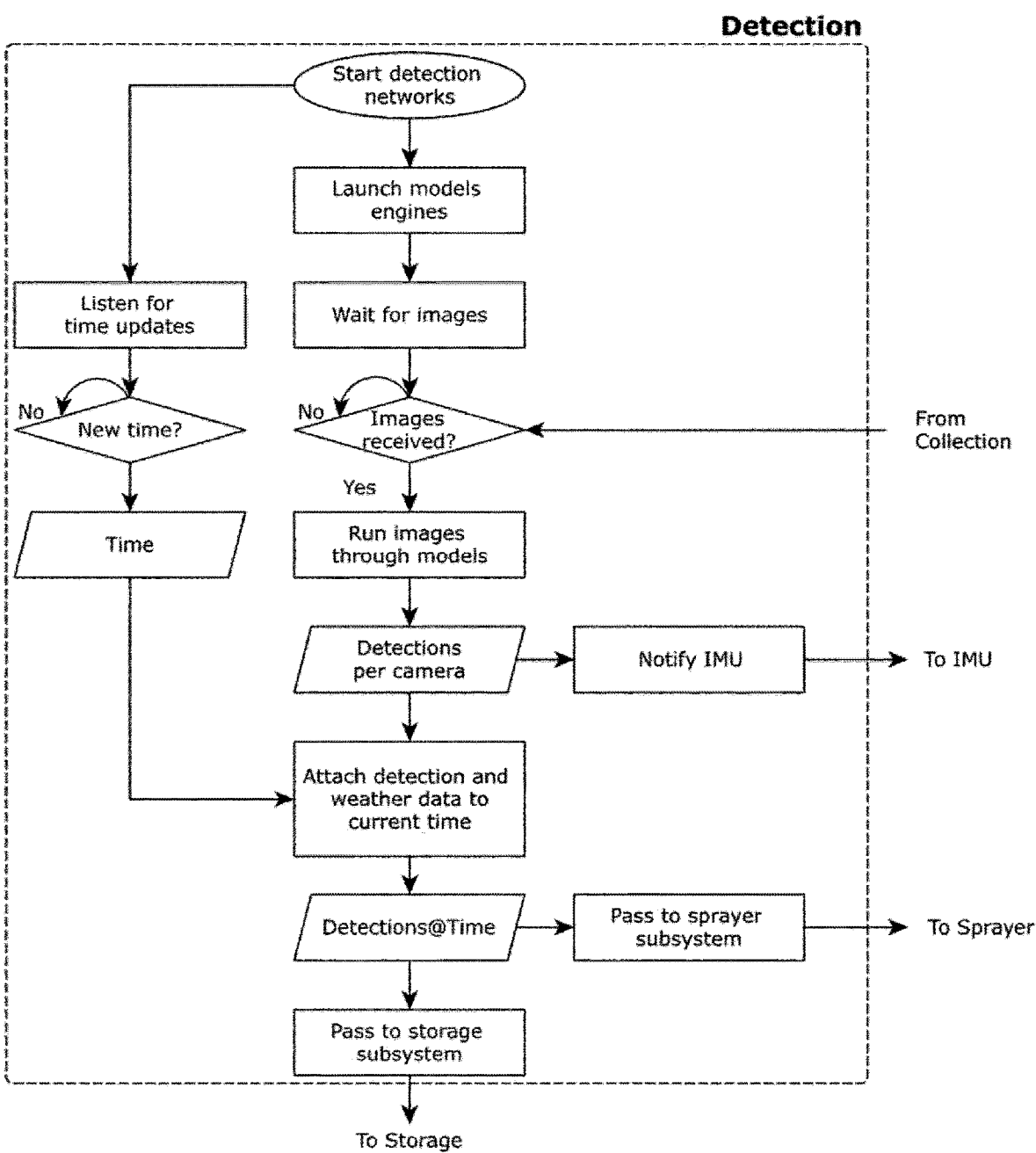
Figure 12E:
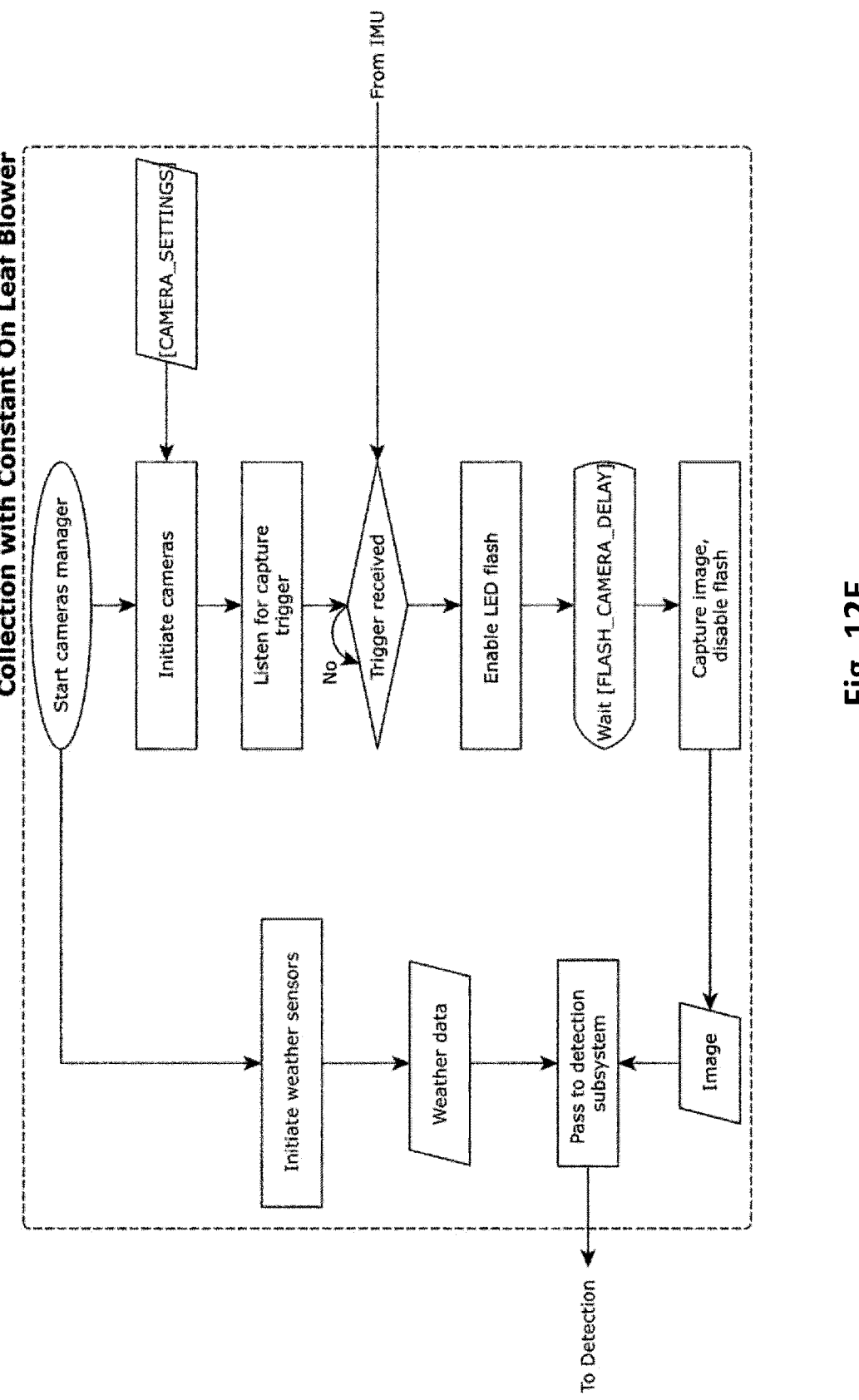
Figure 12F:
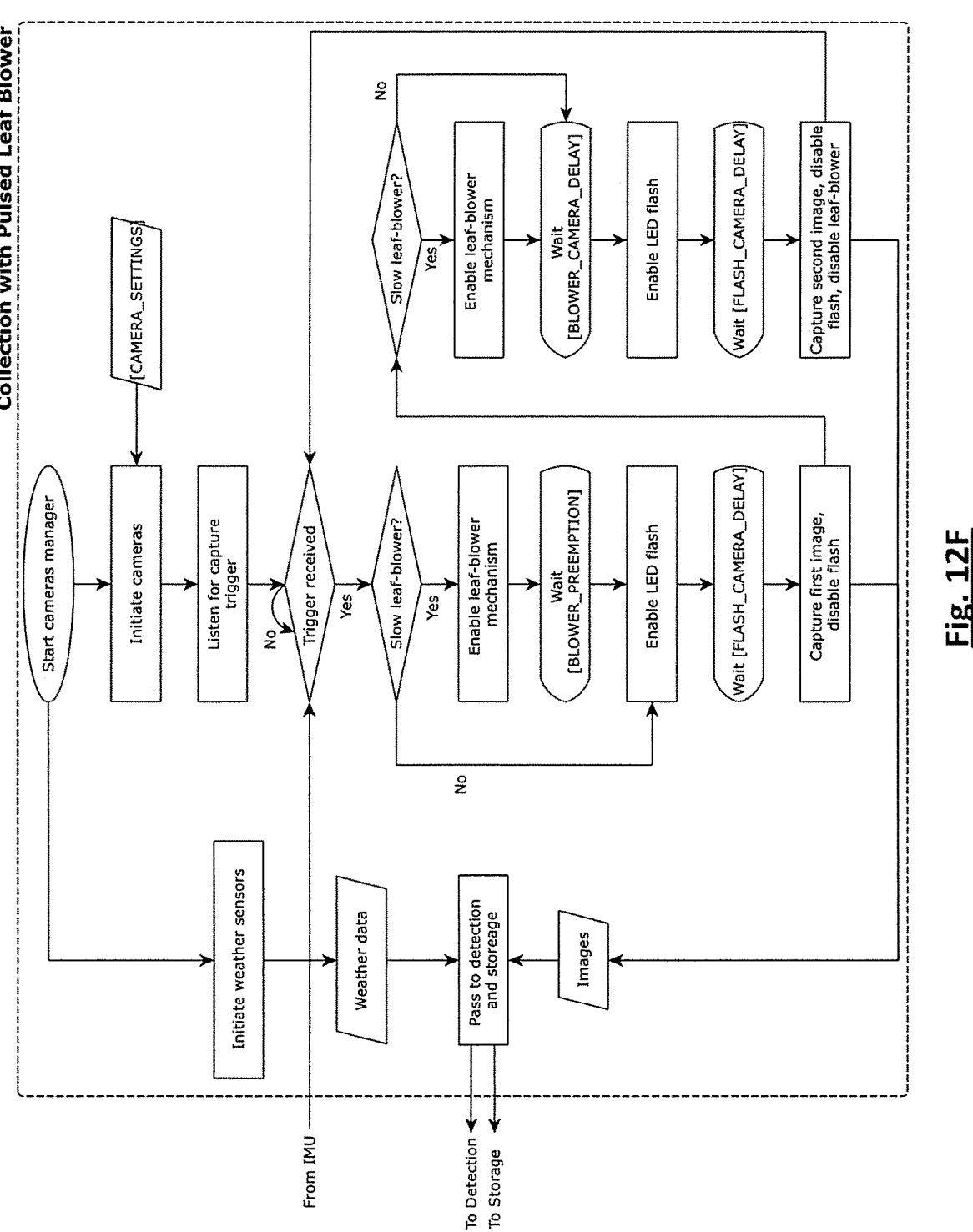
Figure 12G:
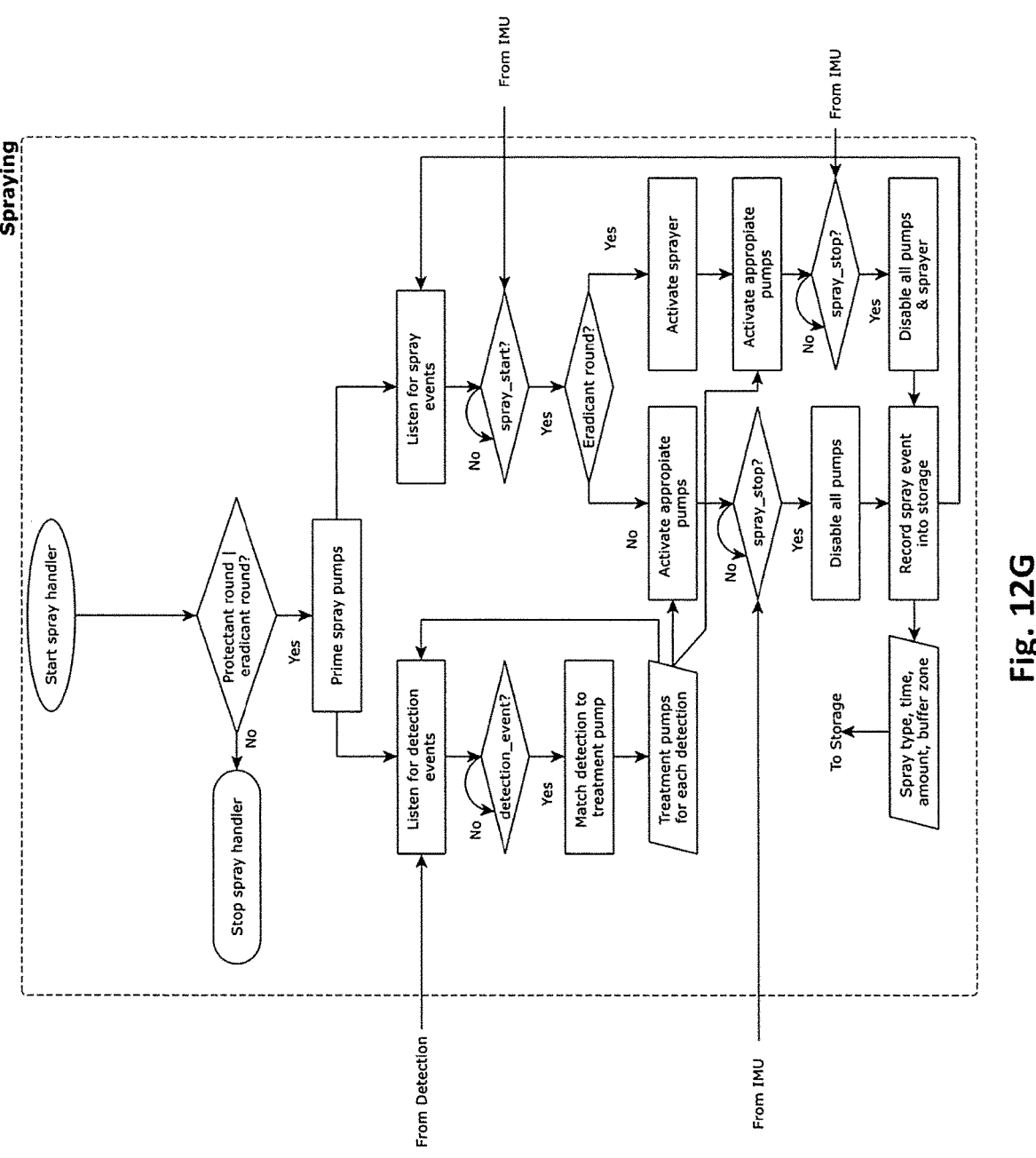

Existing sprayer infrastructure for tall crops usually reaches over the top of a row and/or reaches the other side of the row to ensure good spray penetration, and occasionally spans multiple rows. Sprayers are also generally mounted to the back of a tractor. A large cover would interfere with this spraying process because it couldn't be mounted on the back with the sprayer, and it would be too large to mount on the front without impeding the view of the operator. In the case of putting a cover over the sprayer itself with cameras and lights beneath it, it would become a fumigation tent and the spray would impede the view of the camera. An example implementation for a multi row sprayer is shown in FIGS. 10 and 11. In this case both the image capture device 104 and the blowers 110 are mounted to poles 1002 on the sprayer 112 which extend from the sprayer 112.

Most crop management machinery is mounted to the back of the tractor/vehicle, and again a large cover would impede these processes. A large attachment would not be able to be mounted on the back with other large machinery.

It would be time consuming to install/remove the cover on a day-to-day basis (e.g. switching between multiple tractors/vehicles depending on what crop management operations are to be performed). It may be more appealing to consumers if the device is smaller and easy to install/remove.

In order for spraying to occur simultaneously with detection, the detection process must be done in real time. Real time in that case depends on the requirements of the application. In practical terms, detection and subsequent drive signals for the sprayer must be completed prior to the time it takes for the sensor to image the pest/disease location, until the sprayer nozzles reach the same (or a close) location. This may in some cases require a maximum speed limit of the vehicle.

Alternatively, spraying may occur separately from detection. For example, in a vineyard, protectant spraying is done every 7-10 days and is largely time based, although some growers spray more often following bad weather. In that case, following the vineyard example, the detection data may provide one or more advantages.

Optimising Protectant Spraying Based on Pest/Disease Pressure

Organic growers cannot spray most eradicants as they're largely synthetic products, and organic based eradicants are more expensive and destructive than synthetic ones. Consequently, organic growers opt to "double-down" on protectant spraying when a pest/disease is detected. This translates to both higher concentrations, and a lower spraying interval.

In large vineyards, for example, growers sometimes tighten their intervals instead of spraying eradicant as the agrochemical cost is very expensive per hectare for eradicants.

In general, information regarding pest/disease presence can optimise the process of protectant spraying so that it's not based only on time intervals.

For example, a large vineyard may choose to halt protectant spraying for another few days upon learning that the disease pressure is very low, and that weather is good for the next few days. Or that they may have to spray immediately upon learning that disease pressure is high and that coming weather is unfavourable.

Similarly, an organic grower may decide to "double-down" on more actively infected areas of the crop.

Aid Crop Valuation

Wineries, for example, check their contract grower's vineyards manually near the end of the season; if the grower has 3-5% or more of a powdery mildew/botrytis/downy mildew infection, then the crop is devalued or even rejected entirely.

The process of estimating how much of the crop is affected is done manually by human scouts and suffers from small sample sizes (scouts can't inspect every single vine) and human error in the detection of pests and diseases.

Using one or more embodiments of automated detection may provide historic pest/disease progression information right from the start of the growing season until harvest, thus eliminating any human error and resulting in the objective evaluation of a crop's worth.

Spray Plan Efficacy

Given the lack of coverage by scouts, growers cannot tell if a particular spray plan is successful or not. A spray plan to treat an active infection takes about two days to formulate, meaning the size of the problem area is overestimated to account for diseases spreading during this time.

Using one or more embodiments of automated detection may allow growers to see infection trends over time down to a single vine. This information helps to create efficient and precise spray plans that reduce costs and increase sustainability by reducing agrochemical use.

Log Pest and Disease Occurrence and Treatments

In some places, the only spray evidence growers are required to provide to wineries or regulatory bodies are spray diaries indicating when and what was sprayed. Such honesty-based systems are prone to human error and exploitation. Growers emphasised that as technology evolves, the level of scrutiny and proof for spray evidence and justification will also significantly increase. Most growers are wary of European Union's actions in "cracking down" on agrochemical use, which is forcing (through market access restrictions) other countries to stand in line.

Using one or more embodiments of automated detection may allow thorough and accurate justification for spraying, and geo-tagged dispensing of eradicant. This may allow growers to provide evidence to winegrowing regulatory bodies, down to individual vines. Growers can spray to optimise the health of their crop without worrying about breaching regulations.

Predict and Forecast Crop Performance

By collecting pest and disease information, yield information, and localised weather information over time, machine learning models or statistical analyses can be used to identify trends and correlations between yield, pest and disease pressure, and other environmental factors. These trends and correlations may then be used to predict pest and disease pressure or yield in the future.

Traditional yield estimation techniques involve systematically sampling across the (field, orchard, vineyard) for evidence of crop growth. This is done by dividing the region up and sampling each one. In early stages this can include counting buds, shoots, and more. In later stages this can include counting inflorescences, bunches, fruit and more. This data alongside historical ground truth data of average weights and sizes is used to extrapolate an estimate of yield for each sampled region and then combined to give a total estimate for yield. This sampling is done periodically throughout the growth of the crop, often with weeks or months between sampling. The error in traditional yield estimation techniques is caused by a sampling error both temporally and spatially as well as human error during counting.

Our method decreases the sampling error caused in both respects. The vision and detection system allows for precise counting at a per vine/crop/plant level which can be synthesized with traditional yield estimation techniques to decrease the error caused by sampling. This method can be applied at a higher rate which collects more data to aid with extrapolating yield estimates and removes a large component of the human labour required to count.

Combined with the ability to detect pest and disease, our method is able to precisely identify areas in the field which have had their growth stunted, damaged, or for significant diseases, areas where fruit must be removed by human intervention. This allows us to calibrate the estimated count of a crop at a precise location and time.

A combination of this data and data from other sensors can be used to forecast with higher precision. Current methods either use distant weather stations or little equipment at all to gage key variables that influence yield and disease risk. Temperature and humidity play an integral role in disease forecasting. Our system allows us to measure small variations among microclimates that are known to be created in precise areas across the vineyard. One approach to yield estimation is to count bunches of grapes/berries, or inflorescences (grape "blossoms") and young shoots which will eventually grow bunches on them. With counting inflorescences and shoots, that's a more predictive method of estimating yield, as you won't know how many will actually mature into bunches. This method may require some statistical modelling and historical data of harvest tonnage which is correlated to the number of shoots/inflorescences on each vine.

Counting bunches and berries may be a more concrete way to estimate yield, and the closer this is done to harvest, the more accurate it will be. Things which can affect yield once the berries have matured are pests and diseases, so there's still some prediction that needs to be done in case there's fruit which needs to be discarded.

Estimations of how many bunches there are per vine, can be correlated to their mass so we can estimate the tonnage at harvest. This would need to be done by taking some measurements of bunches and correlating their size and shape to their weight. From there, we'd estimate the size and shape of a bunch from the images (including estimating how big a bunch could be if it's partly occluded) and then estimate the weight.

This information will help growers to:

plan where to discard or drop produce which is unsuitable for harvest view crop output over time plan supply chains for transporting harvested produce estimate the value of the crop before it is harvested create a health history for every plant, block of plants, and the crop as a whole.

receive warnings about plants that are underperforming or at-risk of developing an infection before it actually occurs.

Controller

Because the LED is being strobed, the exposure time configuration, and the physical distances between the moving components, in some applications it may be desirable to have a careful synchronisation between the LED strobe, blower pulse, image detection, and spray application.

Figure 8:
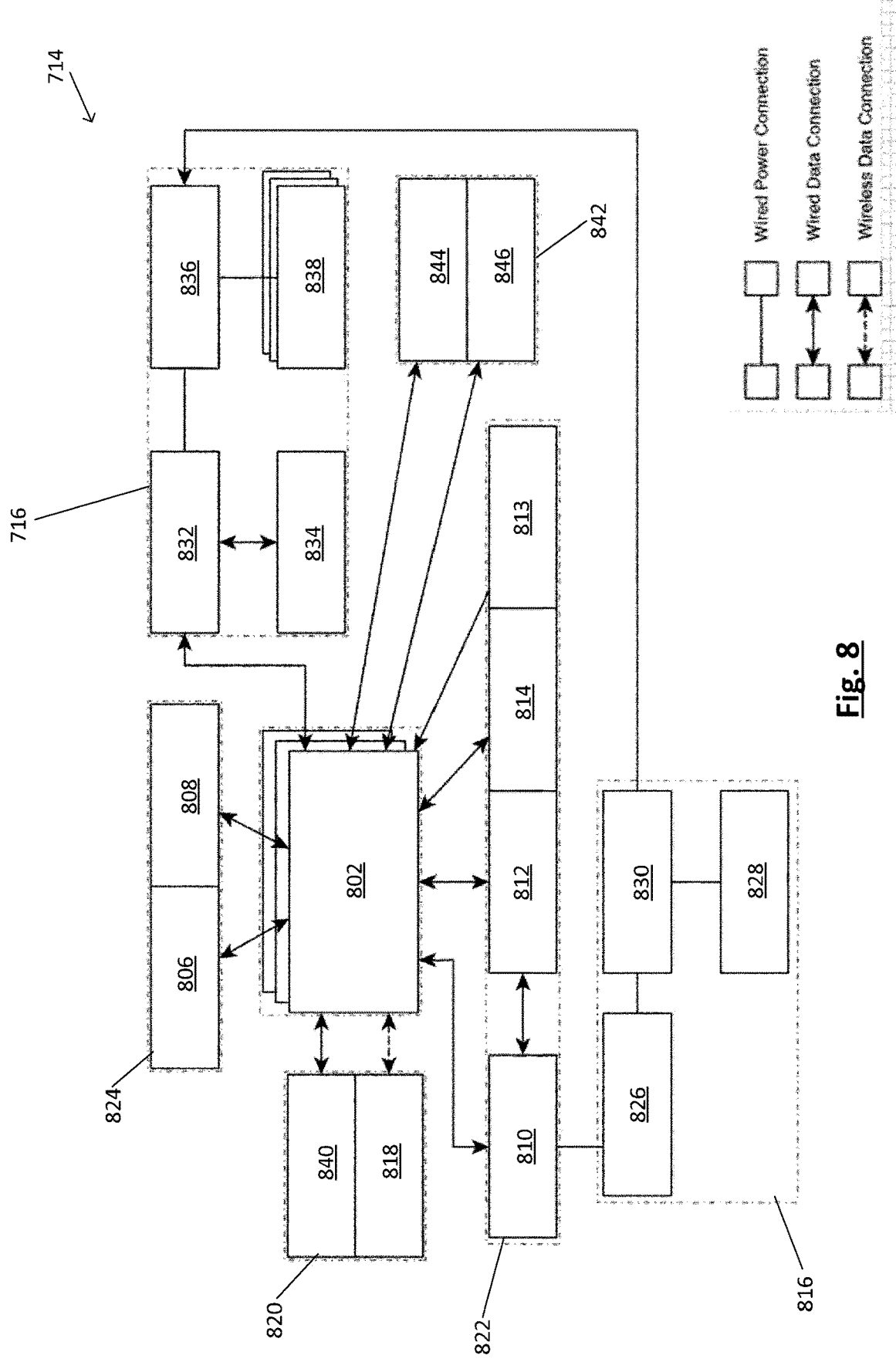
FIG. 8 is a block diagram of the detection controller in FIG. 7.

The synchronisation and other control functions may be implemented using the detection controller 714, a more detailed example of which is shown in FIG. 8. The controller 714 includes a microcontroller, single board computer (SBC) or processor 802, memory, an inertial measurement unit (IMU) 806, Global Navigation Satellite System (GNSS) or Global Positioning System (GPS) 808, LED flash circuit 810, CMOS sensors driver 812, blower controller 814, power supply 816 and spray controller 716.

The SBC or processor 802 is in communication with storage 820, which can employ external storage 840 and a user's phone 818. The LED flash circuit 810, CMOS sensors driver 812, blower controller 814, and weather sensors 813 make up a collection subsystem 822. The power supply 816 includes a 12V vehicle battery 828, a boost converter 826 for outputting 200V, an automotive power regulator 830 for outputting 12V and optionally a buck converter for outputting 5V. The IMU 806 and GNSS/GPS unit 808 make up a positioning subsystem 824. The boost converter may be isolated from vehicle battery 828 for electrical safety, or to reduce interference between it and low power components such as the SBC and signal lines. An automotive power supply may also be used to prevent voltage spikes from the vehicle battery from damaging components or the SBC. The spray controller 716 is made up of a sprayer controller 832, a host sprayer controller 834, a pump driver 836 and one or more reservoir pumps 838. The SBC is also connected to a communication subsystem 842 that includes a cellular module 844 and a module 846 for Wi-Fi and/or Bluetooth communications.

Weather sensors (eg, to monitor temperature and humidity) can help forecast pests and disease pressure more accurately for each block/section of the crop rather than relying on a regional weather forecast, or even to a finer resolution within each block/section. This means pests or diseases may be identified at an earlier stage, or smaller problem areas may be flagged as high-risk and the grower can take pre-emptive actions like applying a preventative chemical, trimming canopies to reduce humidity, etc.

The CMOS sensor may output a digital signal to indicate when the exposure is active (so it will be high for the length of the exposure time, e.g. 20 μs), and this may be used to trigger the flash circuit (so in this case, the camera is "software triggered", and then the flash is triggered by the camera). This signal can be used to trigger or synchronise any actuation, it is not necessarily specific to activating a flash. The sensor's internal delay between the exposure being active and the control signal appearing at the output may vary between different sensors, but is generally in the range of microseconds. The CMOS sensor may contain a signal mode whereby an output is activated prior to the exposure being enabled. Such signal can be used for enabling the flash, and the signal on-time and pre-emption timing can be configured appropriately.

The synchronisation of the data capture and flash may also be implemented using a "hardware trigger"; one signal can be generated by the computer to trigger the camera and the flash, or two signals with a programmed delay can be used (e.g. to make sure the flash is on just before the exposure starts).

The flash mechanism requires time to reach the on state; this is called 'rise-time'. Rise-time comprises the time required to charge the MOSFET gates fully, and signal propagation delays through other logic components of the circuit. Optimal image capture is achieved when the sensor is exposed after the flash is fully on. Therefore, there is a delay between when the flash is enabled and when the sensor is exposed. For example, a rise time of 500 nanoseconds may be suitable.

Figure 17:
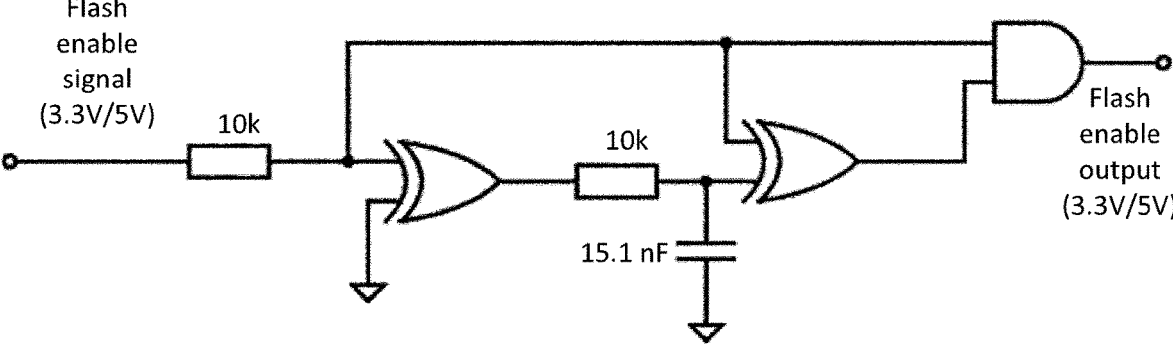
FIG. 17 is a circuit diagram of a filter circuit for the LED control signal

The signal to the LED may need to be "filtered". An example circuit to filter the signal is shown in FIG. 17. The filter may be used to protect the LEDs from accidental over-triggering, e.g. if the camera's GPIO malfunctions, or if the exposure time is set too high (assuming the CMOS sensor triggers the LED), or if there are hardware or software glitches. If the control signal is high for longer than some specified time, e.g. over 300 us, then the filter will pull the control signal low. The example in FIG. 17 uses AND and XOR logic gates and an RC filter, but the same result could be implemented in other ways depending on the requirements of the application e.g. using a 555 timer, in software, or using other configurations of logic gates/circuits.

Figure 24:
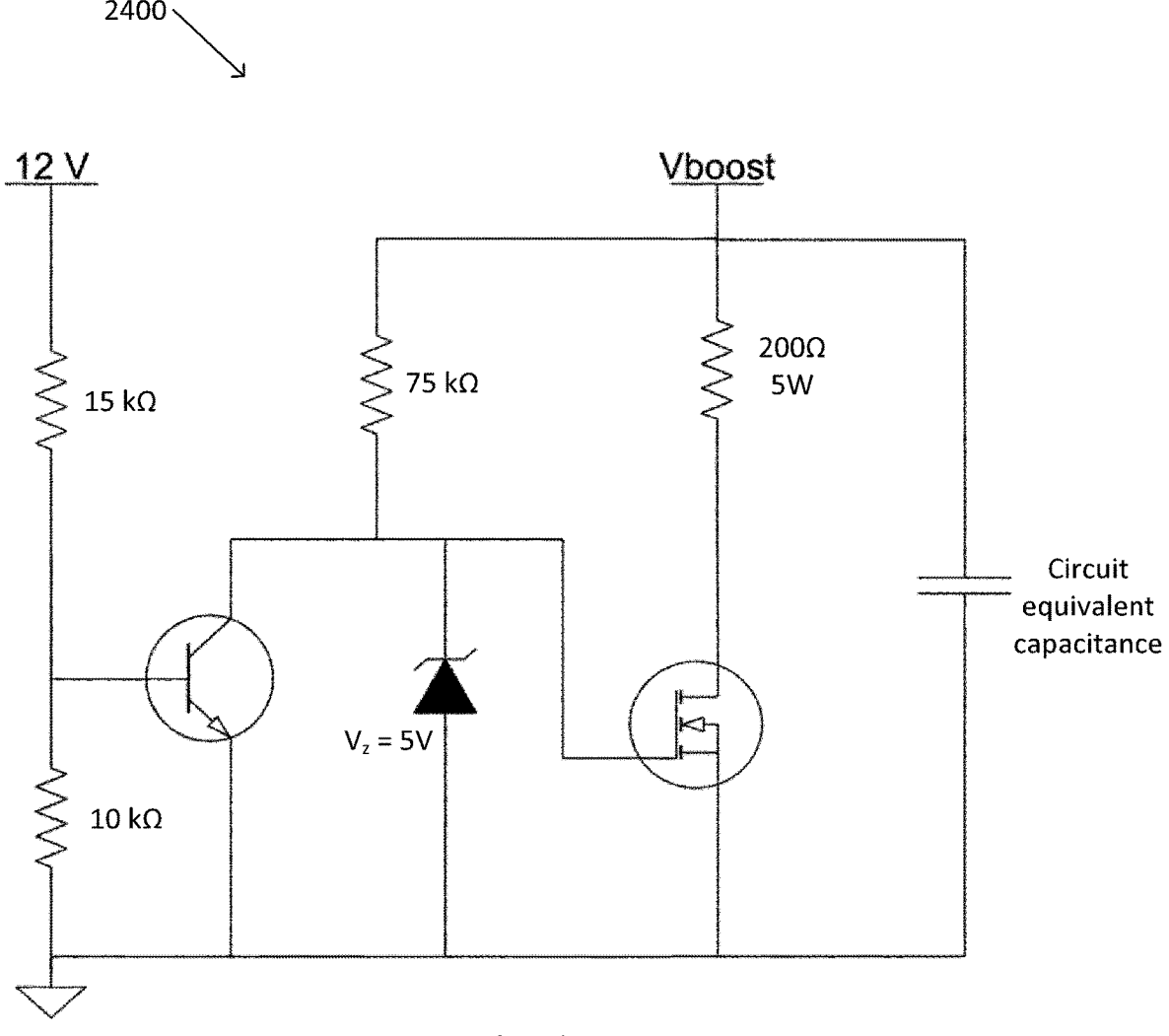
FIG. 24 is a safety discharge circuit according to one embodiment.
Figure 25:
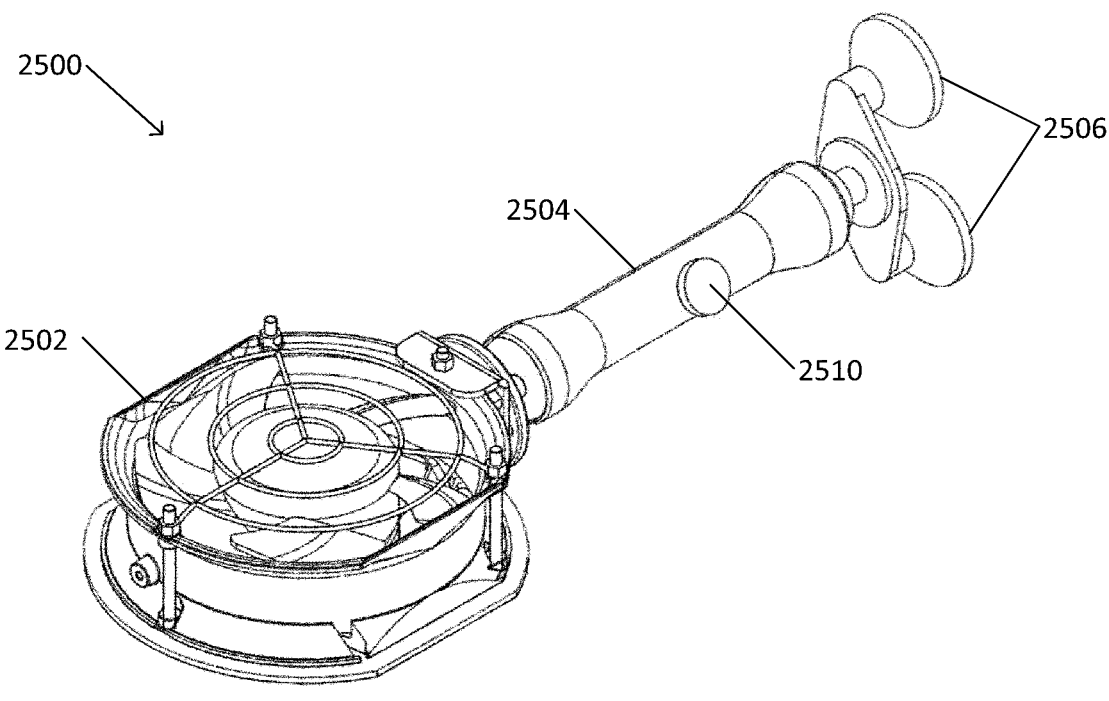
FIG. 25 is a perspective view of a leaf blower according to one example embodiment.
Figure 26:
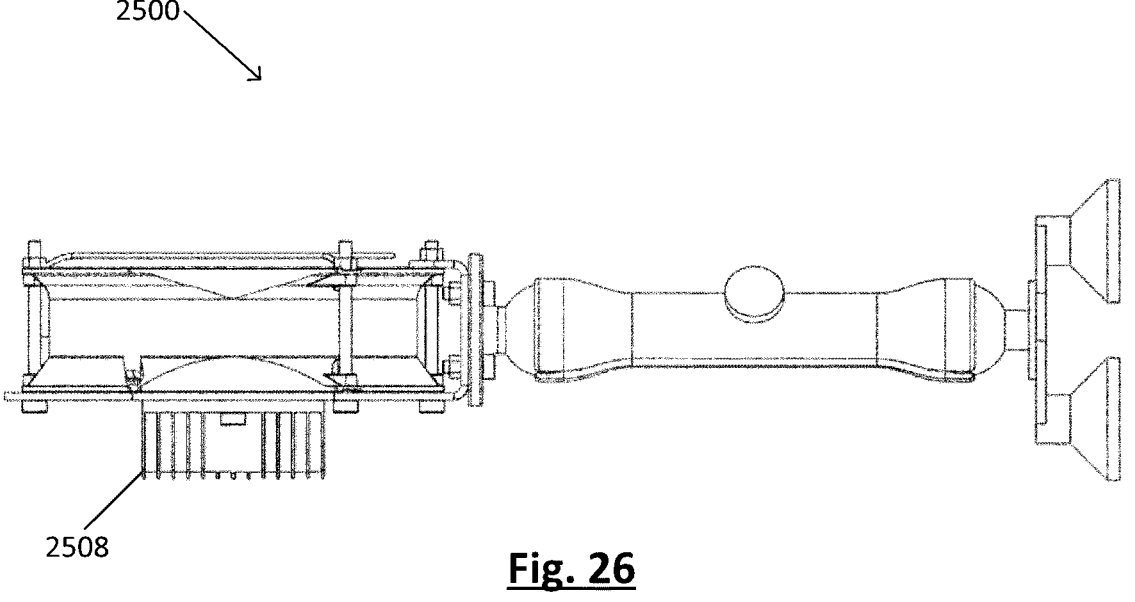
FIG. 26 is a side view of the leaf blower of FIG. 25.
Figure 27:
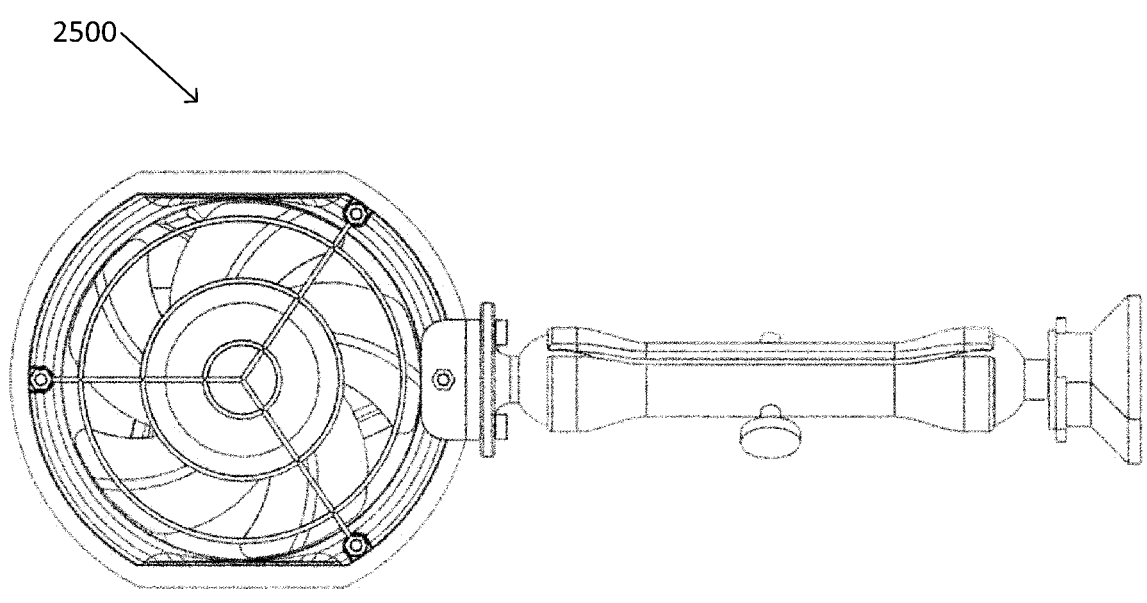
FIG. 27 is front view of the leaf blower of FIG. 25.
Figure 28:
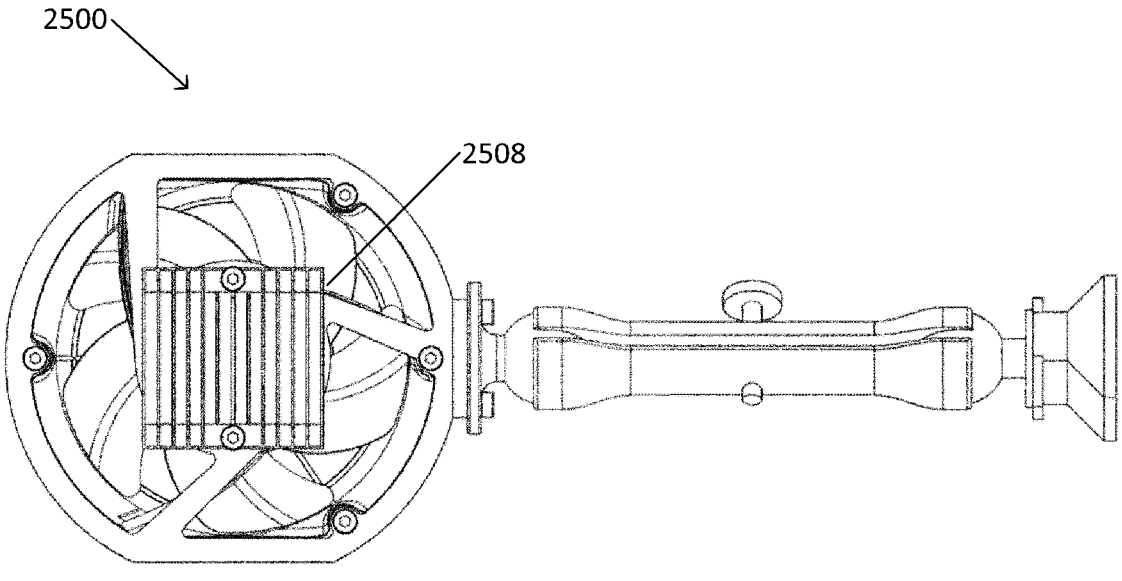
FIG. 28 is a rear view of the leaf blower of FIG. 25.

A safety discharge circuit may also be present in the enclosure to make sure that when the main power is disconnected or the system is powered off, any stored energy in the flash circuit is discharged to a safe level. An example safety discharge circuit 2400 is shown in FIG. 24. There may be multiple ways to implement a safety discharge circuit, including using a depletion mode MOSFET, mechanical switch, relay, or with a high-power bleeder resistor to dissipate the stored energy.

The air blower's purpose is to blow the leaf and show its underside for a subsequent image following an image capture of the overside of the leaf. There is a delay between when the air exits the nozzle and reaches the leaf; this delay is determined by internal factors such as exit velocity, and external factors such as surrounding wind. Ideally, the delay is kept to a minimum, thus collecting a similar photo of the overside/underside. The delay between the first photo and second photo can be minimal such that the two photos largely overlap each other. The first photo capturing the overside of the leaves, and the second photo capturing the underside following the air pulse.

The air pulse may be delivered pre-emptively such that the first photo is taken before the burst of air reaches the leaves, and that the second photo is taken just after the air reaches the leaves. In this case, the leaf blower may be activated 100-200 ms before the first image capture, so that by the second image capture the leaves are displaced by the air, therefore, showing their underside.

Figure 9:
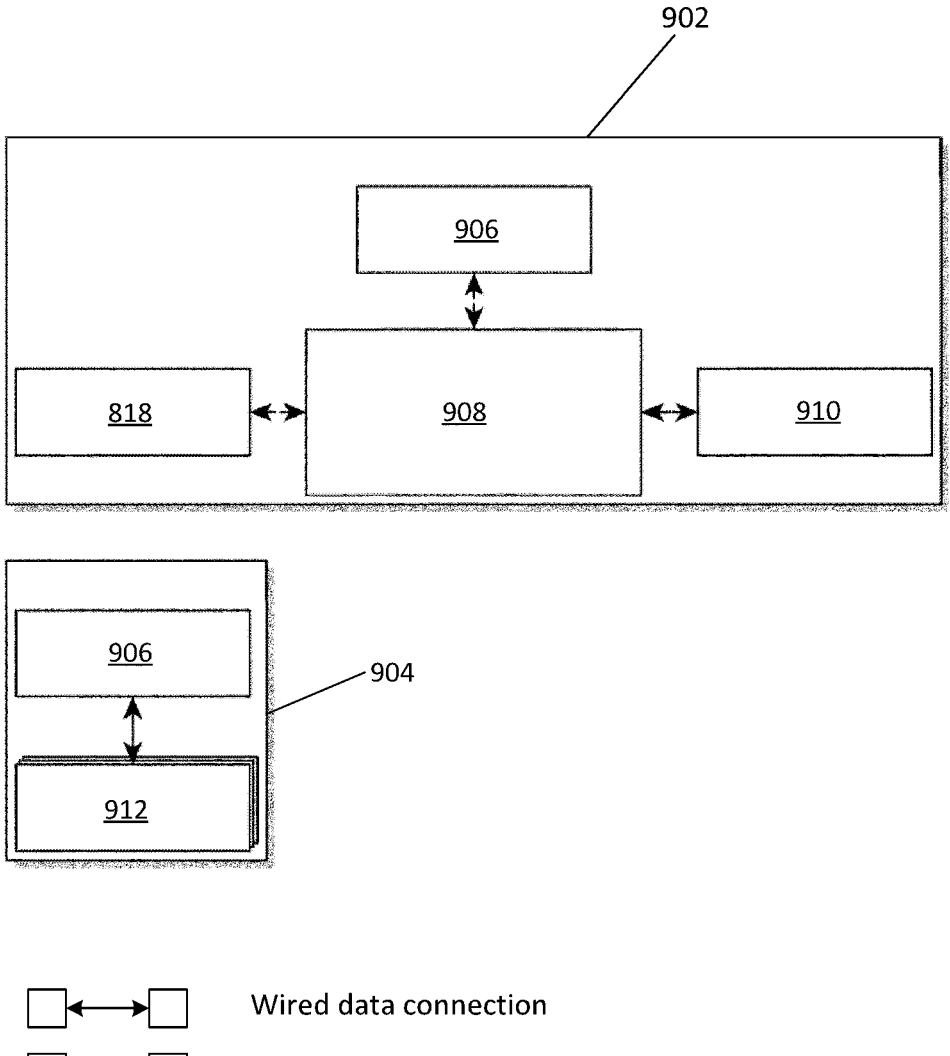
FIG. 9 is a block diagram of the base and cloud controllers.

The controller 714 may communicate with a mobile device 818 or base station 902. The mobile device may include an app designed to transfer the processed data from the rover to the base station 902 for uploading to the cloud 904 via the internet 906, or inputting system parameters such as the buffer zone, or relative positions of system components. The base station 902, shown in more detail in FIG. 9, includes a single-board computer (SBC) or microcontroller 908, and GNSS 910 which is primarily to aid with generating more accurate location data from the GNSS 808 of the rover, and store that together with all other data collected into the cloud 904. Cloud storage and retrieval can be provided using server cluster 912.

Low-power wide-area network technologies such as LoRa or Sigfox may be used to establish a communication link between an internet connected base station and a (the) mobile unit(s) for the purposes of transmitting detection and spray events in real-time to the cloud 904 and/or exchanging GNSS correction information for executing real-time kinematics (RTK) to provide centimetre-level positioning capability for the mobile unit.

RTK requires carrier-phase GNSS information from both the base and the rover. This information is gathered at a certain frequency. The base is stationary while the rover moves; therefore, the rover often operates at a higher frequency than the base. For example, the base may operate at 1 Hz and the rover at 4-10 Hz One option is to use LoRaWAN wireless communication between the base station 902 and the controller 714 to achieve a good real-time kinematic (RTK) location solution. Alternatively, a post-processing kinematic (PPK) solution can be implemented whereby the RAW GNSS measurements can be stored on the tractor/ATV unit (alongside detections) and then uploaded to the cloud over the user's phone (camera system←Bluetooth→User phone←Wi-Fi→Cloud) or through a USB drive (camera system←USB→flash drive←PC→Cloud). The base station may be positioned within 10 km of the rover and is connected to the internet via Wi-Fi/Ethernet to constantly send RAW GNSS measurements to the cloud. The kinematic calculations are done in the cloud to get absolute coordinates of the rover's movement over time.

Bluetooth and/or WiFi connectivity may be used to transfer data from controller 714 to the cloud 904 either directly or via an intermediate device (smartphone, laptop, base station, Wi-Fi Repeater—an alternative to a radio link and applicable if controller 714 is within WiFi reach). For the purposes of: Transmitting detection and spray events to the cloud and/or exchanging GNSS correction information for executing post-processed kinematics (PPK) to provide centimetre-level positioning capability for the mobile unit and/or for sending evidence images to prove the detection visually to users.

Another option is to transfer data from controller 714 to the cloud 904 through cellular means. This includes but is not limited to 4G, 3G, 2G, and LPWAN technologies, such as CAT-M1 or NarrowBand IoT or others. For the purposes of: Transmitting detection or spray events to the cloud and/or exchanging GNSS correction information for executing post-processed kinematics (PPK) to provide centimetre-level positioning capability for the mobile unit and/or for sending evidence images to prove the detection visually to users.

Figure 13A:
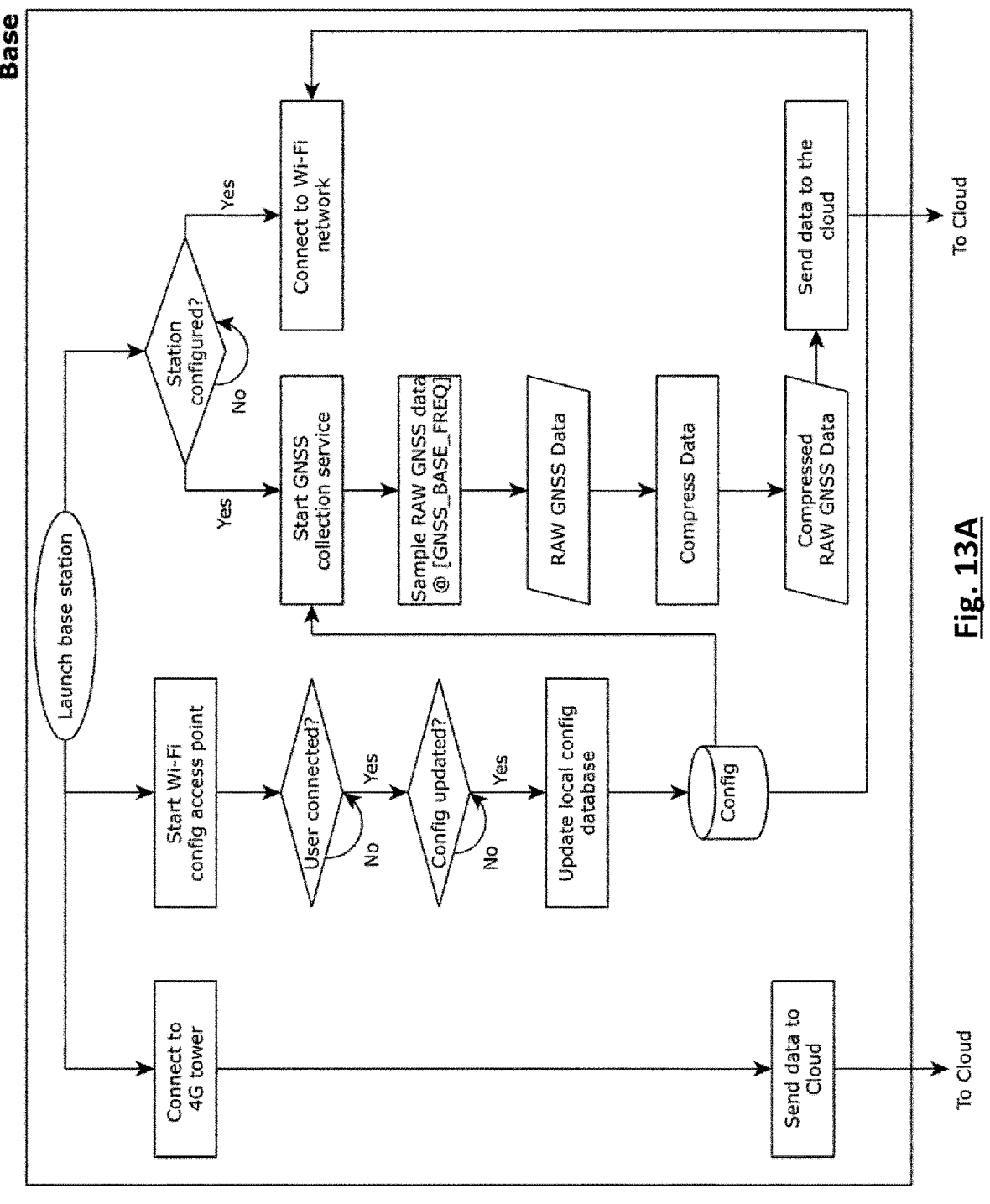
FIGS. 13A-13B are a flowchart of the software processes executed in the base station and cloud to aid with geo-tagging and storage and display of detection and treatment information.
Figure 13B:
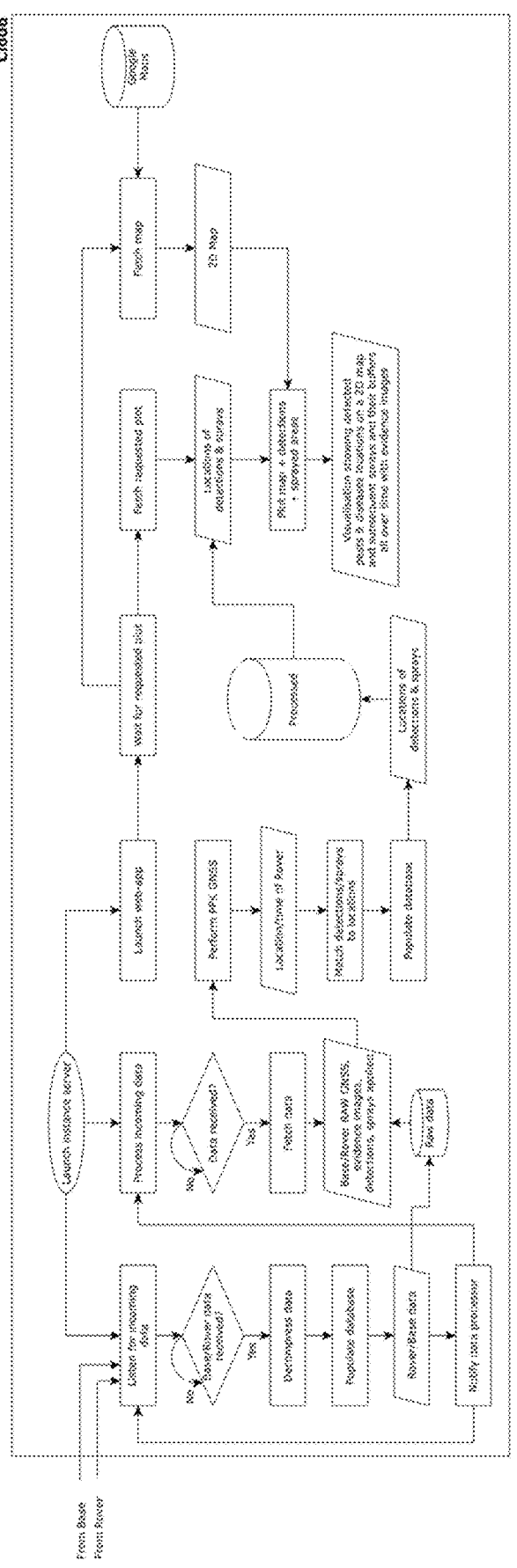

FIGS. 12A-12G show the process followed by the controller 714 to determine location, to collect the image data, to detect pests or disease in the images, to control eradicant spraying, and store the data. FIGS. 13A-13B show the process followed by the base station 902 to acquire and transmit the location data and by the cloud 904 to process the RTK data.

Figure 14:
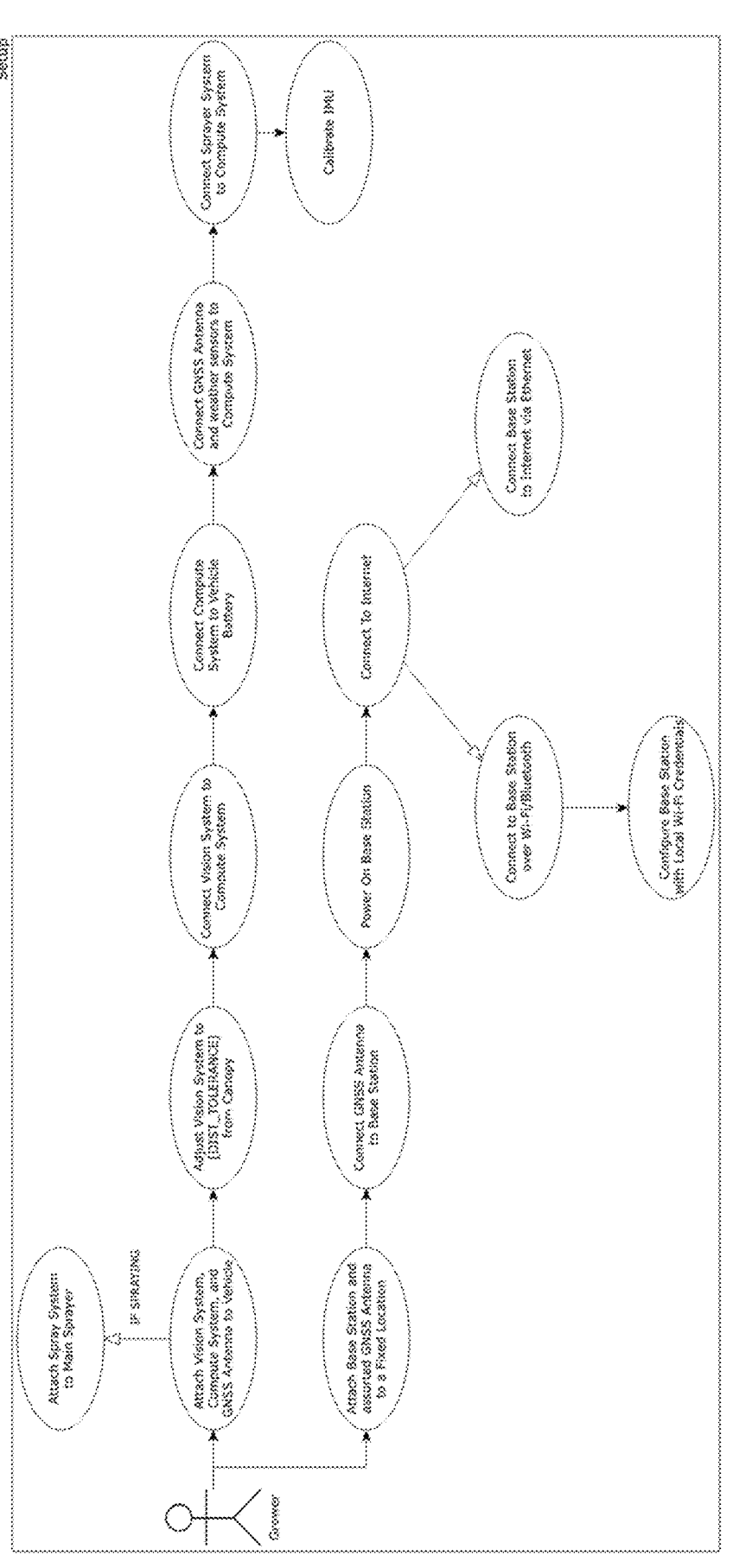
FIG. 14 is a use-case diagram specifying the setup steps of the system.

FIG. 14 shows the use case where a user physically mounts and electrically connects the image capture and spraying system.

Figure 15:
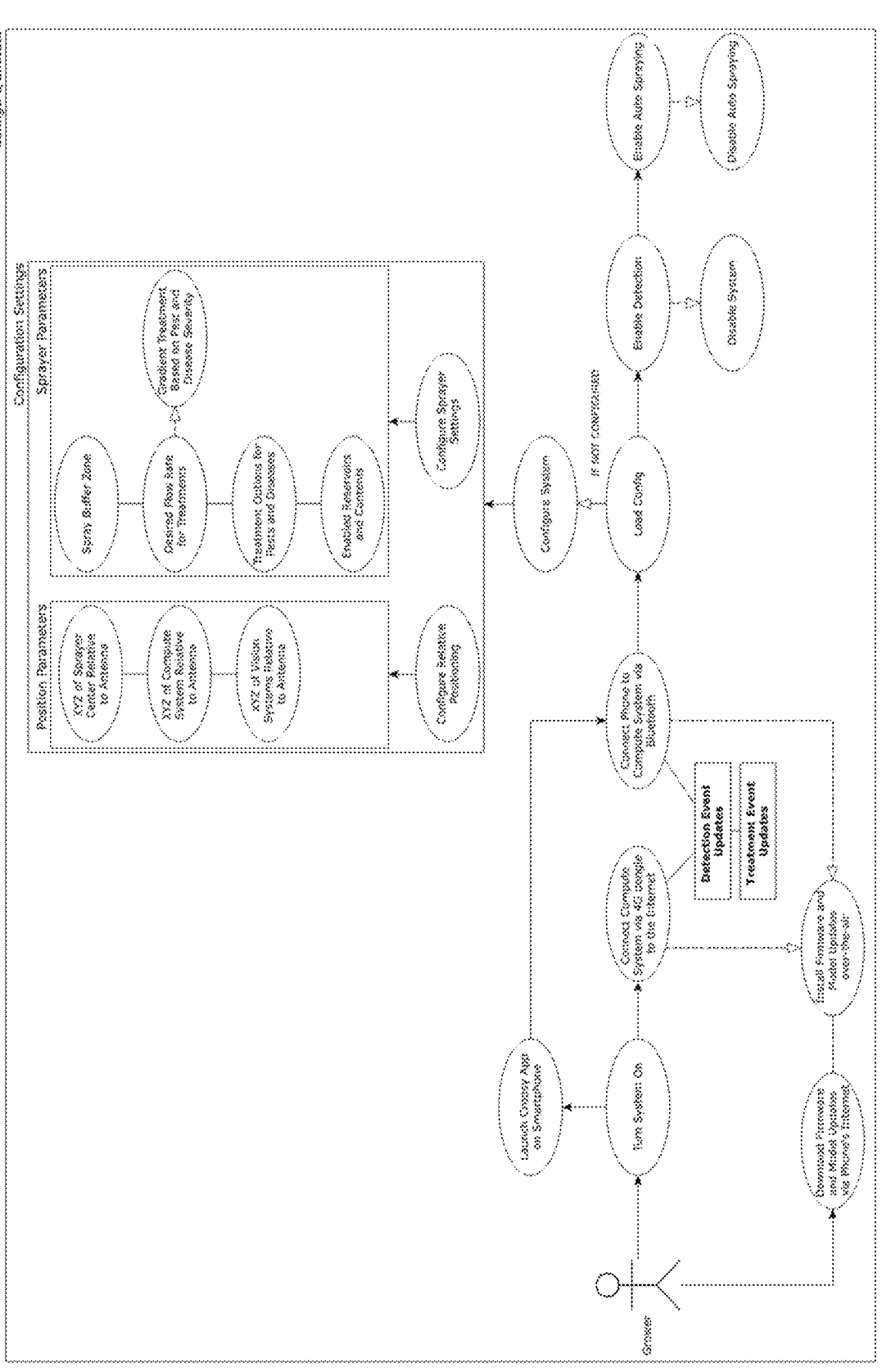
FIG. 15 is a use-case diagram specifying the different user interactions with the system during detection and automated treatment dispensing.

FIG. 15 shows the use case where a user configures the image capture and spraying system. The user must take rough measurements from each camera to the GNSS antenna to determine the x, y, z location of each camera relative to the GNSS antenna. The same must be done for the computation units and the GNSS antenna. Measurement accuracy of +/−15 cm may be sufficient for most applications.

FIG. 16 shows the use case where a user downloads the data to the cloud for post processing, and the insights the user may gain from the data. Insights may include pest and disease occurrence trends over time, pest and disease progression or spread, precise locations of pest and disease occurrence, amount and type of sprays dispensed, current spray plan efficacy, or precise location of sprays dispensed.

In a further embodiment, a user may utilise yield information to optimise the harvesting operations. This includes using the correct number of personnel and harvesters for the number of grapes to be harvested. Also, it includes the positioning optimisations in sending of harvesting personnel and machinery to the correct locations for harvest to minimise unloading time, fuel cost, labour cost, and other cost-related factors.

In a further embodiment, the harvested goods may be optimised using the collected data so that just the right amount of transport vehicles are on-site on a given day to move harvested goods from the harvest personnel and machines to the storage facilities.

In a further embodiment, the storage of harvested fruit may be optimised using the collected data. This may include building extra infrastructure in-case of oversupply. Alternatively or additionally this may include:

Booking the correct amount of storage for the expected yield.

Preventing situations where under-supply leads to over-paying for storage.

Over-supply leading to incurred cost for over-storage.

In a further embodiment, the delivery of enough fruit or processed fruit products to satisfy contractual obligations with produce buyers (e.g. wineries, produce distributors, food manufacturers) may be optimised using the collected data. In the case of under-supply, more fruit can be purchased in-advance to address under-supply, or fruit sold in-advance to address over-supply and improve harvesting, transport, and storage processes.

In a further embodiment, summer pruning processes may be optimised using the collected data. For example, detecting an over-target fruit count results in a targeted fruit dropping where the fruit is cut in the early stages to prevent densification, leading to delayed ripening, increased pests and disease pressure, and others. Another example is shoot-thinning whereby excessive shoots are removed to avoid densification of the canopy with fruit. Densification leads to delayed ripening, increased pests and disease pressure, and others.

In a further embodiment, the orchard or vineyard's harvest order may be optimised using the collected data so that only perfectly ripe fruit is picked—not too early and not too late. This is achieved by measuring each plant's and fruit's growth stages, subsequently harvesting suitable areas just-in-time.

In a further embodiment, the placement of bird-nets to the areas that have reached adequate ripeness may be determined using the collected data. This is achieved by measuring each plant's and fruit's growth stages, placing bird nets or bird deterrents, on sites that passed a suitable growth stage for the respective crop.

In a further embodiment, winter pruning processes may be optimised using the collected data. For example, detecting an over-target bud count results in a targeted pruning approach where canes or spurs are shortened to reduce the number of buds on them. This in-term leads to fewer shoots growing during the season and results in greater control over quality and quantity of fruit.

In a further embodiment, year-year yield information including bud counts, shoot counts, bunch counts, berry counts, and growth stage estimation may be compiled to optimise fertiliser programs and water irrigation processes to improve control over quality and quantity of fruit.

In a further embodiment, year-year yield information including bud counts, shoot counts, bunch counts, berry counts, growth stage estimation, pest and disease detection, may be compiled to optimise spray programs and improve control over quality and quantity of fruit.

In a further embodiment, year-year yield information including bud counts, shoot counts, bunch counts, berry counts, growth stage estimation, pest and disease detection, may be compiled to optimise spray programs to improve scenario planning and risk mitigation.

In a further embodiment, current season data on pest and disease location and severity may be used to allocate and direct personnel to drop fruit which is unsuitable for harvest before harvest machinery is used.

While the present invention has been illustrated by the description of the embodiments thereof, and while the embodiments have been described in detail, it is not the intention of the Applicant to restrict or in any way limit the scope of the appended claims to such detail. Additional advantages and modifications will readily appear to those skilled in the art. Therefore, the invention in its broader aspects is not limited to the specific details, representative apparatus and method, and illustrative examples shown and described. Accordingly, departures may be made from such details without departure from the spirit or scope of the Applicant's general inventive concept.

The invention claimed is:

1. A method of health management of tall plant crop grown using a training system comprising:

activating a strobed or pulsed illumination source to produce illuminating light;

polarising the illuminating light in a first polarisation axis;

illuminating at least part of a tall plant crop with the polarised illuminating light to produce reflected illuminating light;

polarising the reflected illuminating light in a second polarisation axis transverse to the first polarisation axis to produce cross-polarised reflected illuminating light;

capturing an image of at least part of the tall plant crop using the cross-polarised reflected illuminating light; and analysing the captured image to determine a condition of the tall plant crop.

2. The method of claim 1, wherein the first polarisation axis is at approximately 90° to the second polarisation axis.

3. The method of claim 1, wherein the cross-polarised reflected illuminating light has a greater intensity than ambient light that has reflected from the tall plant crop and been polarised in a second polarisation axis transverse to the first polarisation axis and captured along with the image.

4. The method of claim 3, wherein the ambient light comprises sunlight.

5. The method of claim 4, wherein the intensity of the cross-polarised reflected illuminating light is more than 10 times greater than the intensity of the reflected ambient light.

6. The method of claim 1, comprising:

determining if at least part of the tall plant crop requires treatment based on processing the captured image in real-time to determine if any pests or diseases are present in the image.

7. The method of claim 6, wherein said treatment comprises dispensing treatment chemicals on at least part of the tall plant crop in real-time.

8. The method of claim 7, wherein a type and/or quantity of the treatment chemicals dispensed and/or the location on the tall plant crop said treatment chemicals are dispensed is based on the type of pests or diseases determined to be present in the image, the location on the tall plant crop said pests or diseases are determined to be present at or on, and/or a magnitude or extent of the determined presence of said pests or diseases at or on the tall plant crop.

9. The method of claim 1, wherein the condition of the tall plant crop is selected from the group consisting of at least:
  Yield;
  pests or disease present on and/or effecting the tall plant crop;
  location and number of canes, spurs, and/or branches on the tall plant crop;
  growth stage or maturity of the tall plant crop and/or its fruits;
  nutritional deficiency of the tall plant crop, comprising any one or more of:
  nitrogen deficiency, phosphorus deficiency, potassium deficiency, magnesium deficiency, boron deficiency, and/or zinc deficiency;
  location and number of plant suckers;
  location and number of healthy, limp and/or damaged shoots;
  canopy density and/or leaf-area index;
  location and number of untreated pruning cuts;
  moisture level, and/or
  any combination thereof.

10. The method of claim 9, wherein yield is determined either directly, where this includes imaging and counting fruits, berries, bunches, or buds, blossoms, inflorescences which will later turn into fruits, or imaging and counting which fruits are unsuitable for harvest due to pest, disease, or other damage; or indirectly, where this includes estimating yield from counting shoots, identifying the growth stage of the plant or fruits over time to forecast how much of the crop will reach maturity, and using pest and disease information to forecast how much of the crop may be affected.

11. A vehicle-mountable system for health management of tall plant crop grown using a training system, said system comprising:
  an active illumination source configured to produce illuminating light to illuminate a tall plant crop;
  a first polariser arranged to polarise the illuminating light from the active illumination source;
  a second polariser arranged to cross-polarise light reflected from the tall plant crop, the second polariser having a polarisation axis transverse to the polarisation axis of the first polariser; and
  an image capture device configured to capture light cross-polarised by the second polariser;
  an on-board computation unit configured to process images of the light cross-polarised by the second polariser captured by the image capture device in real-time;
  wherein the active illumination source is configured to produce illuminating light of sufficient intensity such that the cross-polarised reflected illuminating light is of greater intensity than ambient light reflected from the tall plant crop and polarised by the second polariser.

12. The system of claim 11, wherein the ambient light comprises sunlight.

13. The system of claim 11, wherein the active illumination source has a total output intensity of at least 1,100,000 lumens, comprises one or more light-emitting diodes and wherein the system is configured to strobe the light-emitting diodes at an intermittent voltage above a rated LED voltage.

14. The system of claim 11, wherein the on-board computation unit is configured to process images captured by the image capture device in real-time so as to determine a condition of the tall plant crop in real time.

15. The system of claim 14, wherein said condition of the tall plant crop comprises any one or more of:
  Yield;
  pests or disease present on and/or effecting the tall plant crop;
  location and number of canes, spurs, and/or branches on the tall plant crop;
  growth stage or maturity of the tall plant crop and/or its fruits;
  nutritional deficiency of the tall plant crop, comprising any one or more of:
  nitrogen deficiency, phosphorus deficiency, potassium deficiency, magnesium deficiency, boron deficiency, and/or zinc deficiency;
  location and number of plant suckers;
  location and number of healthy, limp and/or damaged shoots;
  canopy density and/or leaf-area index;
  location and number of untreated pruning cuts;
  moisture level, and/or
  any combination(s) thereof.

16. The system of 11, wherein the on-board computation unit is configured to process images captured by the image capture device in real-time to determine if any pests or diseases are present in the image so as to thereby determine if at least part of the tall plant crop requires treatment based on said determining of any pests or diseases present in the image.

17. The system of claim 16, wherein said treatment comprises emitting control signals to a sprayer controller of a vehicle-mounted spray system to dispense treatment chemicals on at least part of the tall plant crop in real-time together with and/or after said real-time processing by the board computation unit.

18. The system of claim 17, wherein said control signals comprise an indication of the type and/or quantity of the treatment chemicals to be dispensed and/or an indication of the location on the tall plant crop said treatment chemicals are to be dispensed on based on the type of pests or diseases determined to be present in the image, the location on the tall plant crop said pests or diseases are determined to be present at or on, and/or a magnitude or extent of the determined presence of said pests or diseases at or on the tall plant crop.

19. The system of claim 18, wherein the vehicle-mounted spray system comprises a plurality of reservoirs for different types of treatment chemicals, and said control signals are configured to:
  i) turn certain nozzles of the spray system on and/or off,
  ii) actuate independent motorised pumps in the plurality of reservoirs to feed an appropriate amount of treatment chemicals into a main reservoir line or mixing chamber of the spray system,
  iii) actuate independent motorised pumps in the plurality of reservoirs to feed an appropriate amount of treatment chemicals into certain nozzles of the spray system for targeted spraying, and/or
  iv) synchronise the spraying and/or actuation of the motorised pumps,
  based on the type of pests or diseases determined to be present in the image, the location on the tall plant crop said pests or diseases are determined to be present at or on, and/or a magnitude or extent of the determined presence of said pests or diseases at or on the tall plant crop.

20. A system for health management of tall plant crop grown using a training system, said system comprising:

a vehicle-mountable arrangement comprising:

a polarised high intensity illumination source configured to illuminate foliage or fruit of a target tall plant crop at a plurality of locations along or of said tall plant crop, and a polarised image capture device configured to capture images of the foliage and/or fruit illuminated at said plurality of locations, said high intensity illumination source and image capture device polarised with polarisers oriented transverse to one another; and an on-board computation unit configured to:

(i) process images of the illuminated foliage and/or fruit in real-time together with high accuracy location data to form tall plant image data, and (ii) determine a feature of at least part of the tall plant crop at at least one location of the plurality of locations along or of said tall plant crop based on analysis of said tall plant image data;

the system being configured to determine and recommend plant health management actions for the tall plant crop based on said feature, wherein said feature comprises any one or more of: yield, pests or disease present on and/or effecting the tall plant crop, location and number of canes, spurs, and/or branches on the tall plant crop, growth stage or maturity of the foliage and/or fruit the tall plant crop, nutritional deficiencies, location and number of plant suckers, location and number of healthy, and limp and/or damaged shoots, canopy density and/or leaf-area index, location and number of untreated pruning cuts and/or moisture level.

\* \* \* \* \*